(12) United States Patent
Webster

(10) Patent No.: US 7,852,491 B2
(45) Date of Patent: Dec. 14, 2010

(54) HUMAN-READABLE, BI-STATE ENVIRONMENTAL SENSORS BASED ON MICRO-MECHANICAL MEMBRANES

(75) Inventor: James Randolph Webster, San Jose, CA (US)

(73) Assignee: QUALCOMM MEMS Technologies, Inc., San Diego, CA (US)

( * ) Notice: Subject to any disclaimer, the term of this patent is extended or adjusted under 35 U.S.C. 154(b) by 263 days.

(21) Appl. No.: 12/060,078

(22) Filed: Mar. 31, 2008

(65) Prior Publication Data

US 2009/0244543 A1    Oct. 1, 2009

(51) Int. Cl.
*G01B 9/02* (2006.01)

(52) U.S. Cl. ...................................................... 356/519
(58) Field of Classification Search ................. 356/454, 356/505, 506, 519
See application file for complete search history.

(56) References Cited

U.S. PATENT DOCUMENTS

| | | | |
|---|---|---|---|
| 4,441,791 A | 4/1984 | Hornbeck | |
| 4,571,603 A | 2/1986 | Hornbeck et al. | |
| 4,748,366 A | 5/1988 | Taylor | |
| 4,850,709 A * | 7/1989 | Ban et al. | 356/454 |
| 4,859,060 A | 8/1989 | Katagiri et al. | |
| 4,954,789 A | 9/1990 | Sampsell | |
| 5,083,857 A | 1/1992 | Hornbeck | |
| 5,216,537 A | 6/1993 | Hornbeck | |
| 5,226,099 A | 7/1993 | Mignardi et al. | |
| 5,489,952 A | 2/1996 | Gove et al. | |
| 5,526,172 A | 6/1996 | Kanack | |
| 5,530,240 A | 6/1996 | Larson et al. | |
| 5,550,373 A | 8/1996 | Cole et al. | |
| 5,551,293 A | 9/1996 | Boysel et al. | |
| 5,561,523 A * | 10/1996 | Blomberg et al. | 356/454 |
| 5,629,521 A | 5/1997 | Lee et al. | |
| 5,771,321 A | 6/1998 | Stern | |
| 5,815,141 A | 9/1998 | Phares | |
| 5,894,686 A | 4/1999 | Parker et al. | |
| 5,973,817 A | 10/1999 | Robinson et al. | |
| 5,977,945 A | 11/1999 | Ohshima | |

(Continued)

FOREIGN PATENT DOCUMENTS

DE    38 32 185    3/1990

(Continued)

OTHER PUBLICATIONS

ISR and WO dated Jun. 5, 2009 in PCT/US09/036656.

(Continued)

*Primary Examiner*—Gregory J Toatley
*Assistant Examiner*—Scott M Richey
(74) *Attorney, Agent, or Firm*—Knobbe Martens Olson & Bear LLP

(57) ABSTRACT

An environmental sensing device includes an interferometric modulator which permanently actuates, in a visually-detectable manner, in response to being exposed to a predetermined environmental threshold or condition. The device can include a reactive layer, coating, or proof mass disposed on a movable member of the interferometric modulator. The reactive layer, coating, or proof mass can expand, contract, bend, or otherwise move when exposed to a predefined chemical, level of humidity, temperature threshold, type of radiation, and/or level of mechanical shock, causing the interferometric modulator to collapse and permanently indicate such exposure.

18 Claims, 13 Drawing Sheets

U.S. PATENT DOCUMENTS

| | | | |
|---|---|---|---|
| 6,040,937 | A | 3/2000 | Miles |
| 6,295,048 | B1 | 9/2001 | Ward et al. |
| 6,304,297 | B1 | 10/2001 | Swan |
| 6,307,194 | B1 | 10/2001 | Fitzgibbons et al. |
| 6,323,834 | B1 | 11/2001 | Colgan et al. |
| 6,412,962 | B1 | 7/2002 | Kaspar |
| 6,549,107 | B2 * | 4/2003 | Lim et al. ................ 335/78 |
| 6,617,963 | B1 * | 9/2003 | Watters et al. ........ 340/10.41 |
| 6,650,455 | B2 | 11/2003 | Miles |
| 6,666,561 | B1 | 12/2003 | Blakley |
| 6,674,562 | B1 | 1/2004 | Miles |
| 6,680,792 | B2 | 1/2004 | Miles |
| 6,737,979 | B1 | 5/2004 | Smith et al. |
| 6,776,538 | B2 * | 8/2004 | Whitney et al. ............ 385/94 |
| 6,819,469 | B1 | 11/2004 | Koba |
| 6,829,132 | B2 | 12/2004 | Martin et al. |
| 7,042,643 | B2 | 5/2006 | Miles |
| 7,046,374 | B1 * | 5/2006 | Barbarossa ............. 356/519 |
| 7,123,216 | B1 | 10/2006 | Miles |
| 7,138,984 | B1 | 11/2006 | Miles |
| 7,280,265 | B2 * | 10/2007 | Miles ..................... 359/290 |
| 7,321,417 | B2 | 1/2008 | Bleeker |
| 7,327,510 | B2 | 2/2008 | Cummings et al. |
| 7,330,369 | B2 * | 2/2008 | Tran ........................ 365/151 |
| 7,369,294 | B2 | 5/2008 | Gally et al. |
| 7,388,706 | B2 | 6/2008 | Miles |
| 7,425,453 | B1 * | 9/2008 | Hutchens et al. ......... 436/165 |
| 7,551,287 | B2 * | 6/2009 | Zribi et al. .............. 356/454 |
| 7,623,752 | B2 | 11/2009 | Gally et al. |
| 2002/0075555 | A1 | 6/2002 | Miles |
| 2003/0072070 | A1 | 4/2003 | Miles |
| 2003/0112507 | A1 | 6/2003 | Divelbiss et al. |
| 2003/0117382 | A1 | 6/2003 | Pawlowski et al. |
| 2003/0128197 | A1 | 7/2003 | Turner et al. |
| 2004/0024580 | A1 | 2/2004 | Salmonsen et al. |
| 2005/0001797 | A1 | 1/2005 | Miller et al. |
| 2005/0046919 | A1 | 3/2005 | Taguchi et al. |
| 2005/0068254 | A1 | 3/2005 | Booth |
| 2005/0231855 | A1 * | 10/2005 | Tran ....................... 360/324.1 |
| 2006/0018348 | A1 | 1/2006 | Przybyla et al. |
| 2006/0066503 | A1 | 3/2006 | Sampsell et al. |
| 2006/0066504 | A1 | 3/2006 | Sampsell et al. |
| 2006/0066557 | A1 | 3/2006 | Floyd |
| 2006/0066595 | A1 | 3/2006 | Sampsell et al. |
| 2006/0066596 | A1 | 3/2006 | Sampsell et al. |
| 2006/0066876 | A1 | 3/2006 | Kothari |
| 2006/0067028 | A1 | 3/2006 | Floyd |
| 2006/0077393 | A1 | 4/2006 | Gally et al. |
| 2006/0077521 | A1 | 4/2006 | Gally et al. |
| 2006/0077617 | A1 | 4/2006 | Floyd |
| 2006/0176241 | A1 | 8/2006 | Sampsell |
| 2006/0202933 | A1 * | 9/2006 | Pasch et al. ................ 345/94 |
| 2006/0250337 | A1 | 11/2006 | Miles |
| 2007/0023851 | A1 | 2/2007 | Hartzell et al. |
| 2007/0138391 | A1 | 6/2007 | Garber et al. |
| 2007/0200839 | A1 | 8/2007 | Sampsell |
| 2007/0242008 | A1 | 10/2007 | Cummings |
| 2007/0247406 | A1 | 10/2007 | Zhou et al. |
| 2008/0112031 | A1 | 5/2008 | Gally et al. |
| 2008/0196814 | A1 | 8/2008 | Yang |
| 2009/0009847 | A1 | 1/2009 | Sasagawa et al. |
| 2009/0141286 | A1 | 6/2009 | Kothari |
| 2009/0207473 | A1 | 8/2009 | Bita et al. |
| 2009/0244679 | A1 | 10/2009 | Khazeni |
| 2009/0244680 | A1 * | 10/2009 | Webster ................... 359/238 |
| 2009/0244681 | A1 * | 10/2009 | Webster ................... 359/238 |
| 2009/0244683 | A1 | 10/2009 | Lan |
| 2009/0267869 | A1 | 10/2009 | Gally et al. |
| 2009/0267953 | A1 | 10/2009 | Sampsell et al. |
| 2009/0308452 | A1 | 12/2009 | Sasagawa et al. |
| 2010/0117761 | A1 | 5/2010 | Floyd |
| 2010/0123706 | A1 | 5/2010 | Lan |
| 2010/0149722 | A1 | 6/2010 | Floyd |

FOREIGN PATENT DOCUMENTS

| | | |
|---|---|---|
| EP | 0 649 010 | 4/1995 |
| EP | 0 725 380 | 8/1996 |
| EP | 1 126 278 | 8/2001 |
| EP | 1 640 323 | 3/2006 |
| EP | 1 640 332 | 3/2006 |
| JP | 2002 287047 | 2/2003 |
| WO | WO 03/056367 | 7/2003 |
| WO | WO 2004/066256 | 8/2004 |
| WO | WO 2004/068460 | 8/2004 |
| WO | WO 2005/066596 | 7/2005 |

OTHER PUBLICATIONS

Miles, "A New Reflective FPD Technology Using Interferometric Modulation," Journal of the SID 5/4, 1997, pp. 379-382.

Miles et al., 10.1: Digital Paper™ for reflective displays, SID 02 Digest, pp. 115-117, 2002.

Winton, John M., "A novel way to capture solar energy," Chemical Week, pp. 17-18 (May 15, 1985).

Wu, "Design of a Reflective Color LCD Using Optical Interference Reflectors," ASIA Display '95, pp. 929-931 (Oct. 16, 1995).

Mark W. Miles, "MEMS-based interferometric modulator for display applications," Proceedings of SPIE, vol. 3876, Aug. 1999, pp. 20-28.

Office Action dated Mar. 16, 2010 in U.S. Appl. No. 12/060,041.

ISR and WO dated Mar. 2, 2010 in PCT/US09/036653.

Brank et al., Sep. 2001, RF MEMS-based tunable filters, International Journal of RF and Microwave Computer-Aided Engineering, 11(5):276-284.

* cited by examiner

|  | Column Output Signals | |
|---|---|---|
|  | $+V_{bias}$ | $-V_{bias}$ |
| Row Output Signals  0 | Stable | Stable |
| $+\Delta V$ | Relax | Actuate |
| $-\Delta V$ | Actuate | Relax |

HUMAN-READABLE, BI-STATE ENVIRONMENTAL SENSORS BASED ON MICRO-MECHANICAL MEMBRANES

BACKGROUND

1. Field of the Invention

The present invention relates to microelectromechanical systems (MEMS).

2. Description of the Related Art

Microelectromechanical systems (MEMS) include micro mechanical elements, actuators, and electronics. Micromechanical elements may be created using deposition, etching, and/or other micromachining processes that etch away parts of substrates and/or deposited material layers or that add layers to form electrical and electromechanical devices. One type of MEMS device is called an interferometric modulator. As used herein, the term interferometric modulator or interferometric light modulator refers to a device that selectively absorbs and/or reflects light using the principles of optical interference. In certain embodiments, an interferometric modulator may comprise a pair of conductive plates, one or both of which may be transparent and/or reflective in whole or part and capable of relative motion upon application of an appropriate electrical signal. In a particular embodiment, one plate may comprise a stationary layer deposited on a substrate and the other plate may comprise a metallic membrane separated from the stationary layer by an air gap. As described herein in more detail, the position of one plate in relation to another can change the optical interference of light incident on the interferometric modulator. Such devices have a wide range of applications, and it would be beneficial in the art to utilize and/or modify the characteristics of these types of devices so that their features can be exploited in improving existing products and creating new products that have not yet been developed.

SUMMARY

In one aspect, a sensor comprises an interferometric modulator which is configured to permanently actuate in response to a presence of at least one selected chemical, wherein the actuation of the interferometric modulator is visually detectable.

In another aspect, a sensor comprises means for interferometrically modulating light and means for inducing permanent actuation of the light modulating means in response to a presence of at least one selected chemical.

In another aspect, a display comprising an array of sensors, where each sensor comprises an interferometric modulator which is configured to permanently actuate in response to a presence of at least one selected chemical, wherein the actuation of the interferometric modulator is visually detectable.

In another aspect, a method of manufacturing an interferometric modulator is provided. The method comprises providing a reactive layer on a movable member of the interferometric modulator, the reactive layer being configured to deform sufficiently to cause the interferometric modulator to collapse when exposed to a predetermined chemical. The method also comprises treating the movable member or an optical stack of the interferometric modulator so as to ensure that adhesion will be permanent upon collapse.

In another aspect, a method of indicating exposure to an environmental stimulus is provided. The method comprises providing an interferometric modulator having a reactive layer disposed on a movable member of the interferometric modulator, the reactive layer being configured to deform in response to being exposed to a predetermined chemical by an amount sufficient to cause the interferometric modulator to collapse, the interferometric modulator being configured to ensure that said collapse is permanent.

In another aspect, a sensor comprises an interferometric modulator which is configured to permanently actuate in response to a predetermined level of mechanical shock, wherein the actuation of the interferometric modulator is visually detectable.

In another aspect, a sensor comprises means for interferometrically modulating light and means for inducing permanent actuation of the light modulating means in response to a predetermined level of mechanical shock.

In another aspect, a display comprises an array of sensors, where each sensor comprises an interferometric modulator which is configured to permanently actuate in response to a predetermined level of mechanical shock, wherein the actuation of the interferometric modulator is visually detectable.

In another aspect, a method of manufacturing an interferometric modulator is provided. The method comprises providing a proof mass on a movable member of the interferometric modulator, the proof mass being configured to cause the interferometric modulator to collapse when exposed to a predetermined level of mechanical shock. The method further comprises treating the movable member or an optical stack of the interferometric modulator so as to ensure that adhesion will be permanent upon collapse.

In another aspect, a method of indicating exposure to an environmental stimulus is provided. The method comprises providing an interferometric modulator having a proof mass disposed on a movable member of the interferometric modulator, the proof mass being configured to cause the interferometric modulator to collapse when exposed to a predetermined level of shock, the interferometric modulator being configured to ensure that said collapse is permanent.

In another aspect, a sensor comprises an interferometric modulator which is configured to permanently actuate when exposed to a predefined level of radiation, wherein the actuation of the interferometric modulator is visually detectable.

In another aspect, a sensor comprises means for interferometrically modulating light and means for inducing permanent actuation of the light modulating means in response to a predefined level of radiation.

In another aspect, a display comprises an array of sensors, where each sensor comprises an interferometric modulator which is configured to permanently actuate when exposed to a predefined level of radiation, wherein the actuation of the interferometric modulator is visually detectable.

In another aspect, a method of manufacturing an interferometric modulator is provided. The method comprises providing a reactive layer on a movable member of the interferometric modulator, the reactive layer being configured to deform sufficiently to cause the interferometric modulator to collapse when exposed to a predetermined level of radiation. The method further comprises treating the movable member or an optical stack of the interferometric modulator so as to ensure that adhesion will be permanent upon collapse.

In another aspect, a method of indicating exposure to an environmental stimulus is provided. The method comprises providing an interferometric modulator having a reactive layer disposed on a movable member of the interferometric modulator, the reactive layer being configured to deform when exposed to a predetermined level of radiation by an amount sufficient to cause the interferometric modulator to collapse, the interferometric modulator being configured to ensure that said collapse is permanent.

In another aspect, a sensor includes an interferometric modulator which is configured to permanently actuate in response to exposure to a predetermined combination of a first environmental stimulus and a second environmental stimulus.

In another aspect, a sensor comprises means for interferometrically modulating light, means for inducing collapse of the light modulating means in response to a first predefined environmental condition, and means for ensuring that said collapse is permanent if said collapse occurs in the presence of a second predefined environmental condition.

In another aspect, a display comprises an array of sensors, where each sensor includes an interferometric modulator which is configured to permanently actuate in response to exposure to a predetermined combination of a first environmental stimulus and a second environmental stimulus.

DETAILED DESCRIPTION OF PREFERRED EMBODIMENTS

The following detailed description is directed to certain specific embodiments of the invention. However, the invention can be embodied in a multitude of different ways. In this description, reference is made to the drawings wherein like parts are designated with like numerals throughout. As will be apparent from the following description, the embodiments may be implemented in any device that is configured to display an image, whether in motion (e.g., video) or stationary (e.g., still image), and whether textual or pictorial. More particularly, it is contemplated that the embodiments may be implemented in or associated with a variety of electronic devices such as, but not limited to, mobile telephones, wireless devices, personal data assistants (PDAs), hand-held or portable computers, GPS receivers/navigators, cameras, MP3 players, camcorders, game consoles, wrist watches, clocks, calculators, television monitors, flat panel displays, computer monitors, auto displays (e.g., odometer display, etc.), cockpit controls and/or displays, display of camera views (e.g., display of a rear view camera in a vehicle), electronic photographs, electronic billboards or signs, projectors, architectural structures, packaging, and aesthetic structures (e.g., display of images on a piece of jewelry). MEMS devices of similar structure to those described herein can also be used in non-display applications such as in electronic switching devices.

MEMS structures can be configured to deform and collapse when exposed to a given environmental condition or set of conditions. Depending on the adhesion forces involved, collapse can result in permanent adhesive failure, or "stiction," in the structure. Although stiction is generally an undesirable trait in these devices, the tendency of certain structures to fail due to stiction under specific conditions can be used to advantage. MEMS devices are described herein which are configured to collapse and achieve permanent stiction when exposed to a predetermined environmental condition or set of conditions. These devices may comprise interferometric modulators which, given their strong optical response upon collapse, are capable of indicating to an observer, in a non-reversible fashion and without the need for external sensing devices, whether the device has been exposed to the predetermined environmental condition or set of conditions at some point in the past. Such devices can be used in various applications, such as consumer-level packaging where conditions during shipping and/or storage must be monitored to ensure quality.

Figure 1:
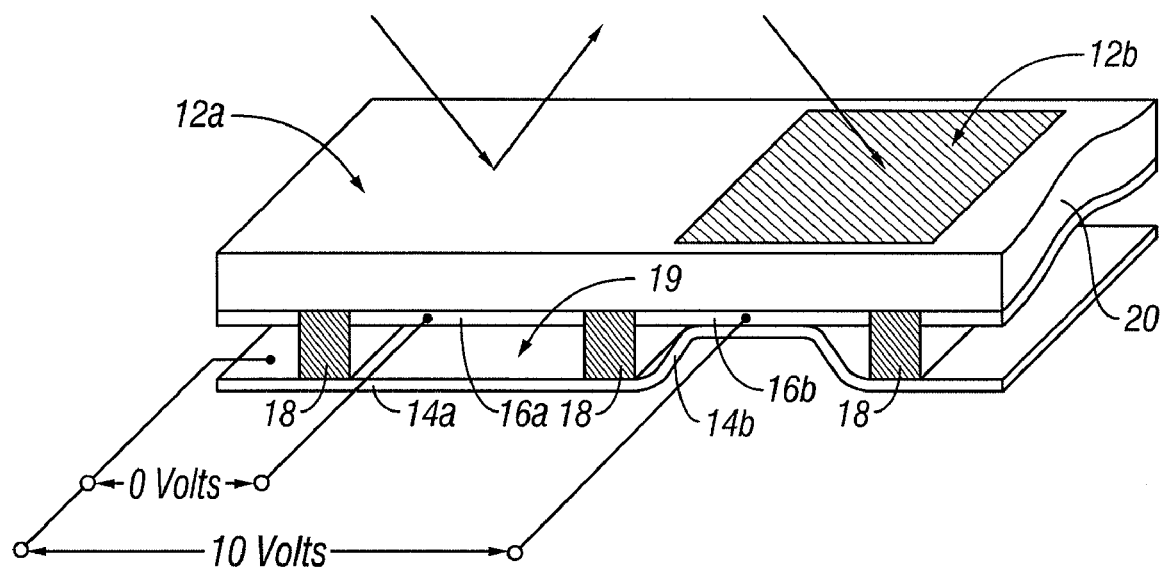
FIG. 1 is an isometric view depicting a portion of one embodiment of an interferometric modulator display in which a movable reflective layer of a first interferometric modulator is in a relaxed position and a movable reflective layer of a second interferometric modulator is in an actuated position.

One interferometric modulator display embodiment comprising an interferometric MEMS display element is illustrated in FIG. 1. In these devices, the pixels are in either a bright or dark state. In the bright ("on" or "open") state, the display element reflects a large portion of incident visible light to a user. When in the dark ("off" or "closed") state, the display element reflects little incident visible light to the user.

Depending on the embodiment, the light reflectance properties of the "on" and "off" states may be reversed. MEMS pixels can be configured to reflect predominantly at selected colors, allowing for a color display in addition to black and white.

FIG. 1 is an isometric view depicting two adjacent pixels in a series of pixels of a visual display, wherein each pixel comprises a MEMS interferometric modulator. In some embodiments, an interferometric modulator display comprises a row/column array of these interferometric modulators. Each interferometric modulator includes a pair of reflective layers positioned at a variable and controllable distance from each other to form a resonant optical gap with at least one variable dimension. In one embodiment, one of the reflective layers may be moved between two positions. In the first position, referred to herein as the relaxed position, the movable reflective layer is positioned at a relatively large distance from a fixed partially reflective layer. In the second position, referred to herein as the actuated position, the movable reflective layer is positioned more closely adjacent to the partially reflective layer. Incident light that reflects from the two layers interferes constructively or destructively depending on the position of the movable reflective layer, producing either an overall reflective or non-reflective state for each pixel.

The depicted portion of the pixel array in FIG. 1 includes two adjacent interferometric modulators 12a and 12b. In the interferometric modulator 12a on the left, a movable reflective layer 14a is illustrated in a relaxed position at a predetermined distance from an optical stack 16a, which includes a partially reflective layer. In the interferometric modulator 12b on the right, the movable reflective layer 14b is illustrated in an actuated position adjacent to the optical stack 16b.

The optical stacks 16a and 16b (collectively referred to as optical stack 16), as referenced herein, typically comprise several fused layers, which can include an electrode layer, such as indium tin oxide (ITO), a partially reflective layer, such as chromium, and a transparent dielectric. The optical stack 16 is thus electrically conductive, partially transparent, and partially reflective, and may be fabricated, for example, by depositing one or more of the above layers onto a transparent substrate 20. The partially reflective layer can be formed from a variety of materials that are partially reflective such as various metals, semiconductors, and dielectrics. The partially reflective layer can be formed of one or more layers of materials, and each of the layers can be formed of a single material or a combination of materials.

In some embodiments, the layers of the optical stack 16 are patterned into parallel strips, and may form row electrodes in a display device as described further below. The movable reflective layers 14a, 14b may be formed as a series of parallel strips of a deposited metal layer or layers (orthogonal to the row electrodes of 16a, 16b) deposited on top of posts 18 and an intervening sacrificial material deposited between the posts 18. When the sacrificial material is etched away, the movable reflective layers 14a, 14b are separated from the optical stacks 16a, 16b by a defined gap 19. A highly conductive and reflective material such as aluminum may be used for the reflective layers 14, and these strips may form column electrodes in a display device.

With no applied voltage, the gap 19 remains between the movable reflective layer 14a and optical stack 16a, with the movable reflective layer 14a in a mechanically relaxed state, as illustrated by the pixel 12a in FIG. 1. However, when a potential difference is applied to a selected row and column, the capacitor formed at the intersection of the row and column electrodes at the corresponding pixel becomes charged, and electrostatic forces pull the electrodes together. If the voltage is high enough, the movable reflective layer 14 is deformed and is forced against the optical stack 16. A dielectric layer (not illustrated in this Figure) within the optical stack 16 may prevent shorting and control the separation distance between layers 14 and 16, as illustrated by pixel 12b on the right in FIG. 1. The behavior is the same regardless of the polarity of the applied potential difference. In this way, row/column actuation that can control the reflective vs. non-reflective pixel states is analogous in many ways to that used in conventional LCD and other display technologies.

FIGS. 2 through 5B illustrate one exemplary process and system for using an array of interferometric modulators in a display application.

Figure 2:
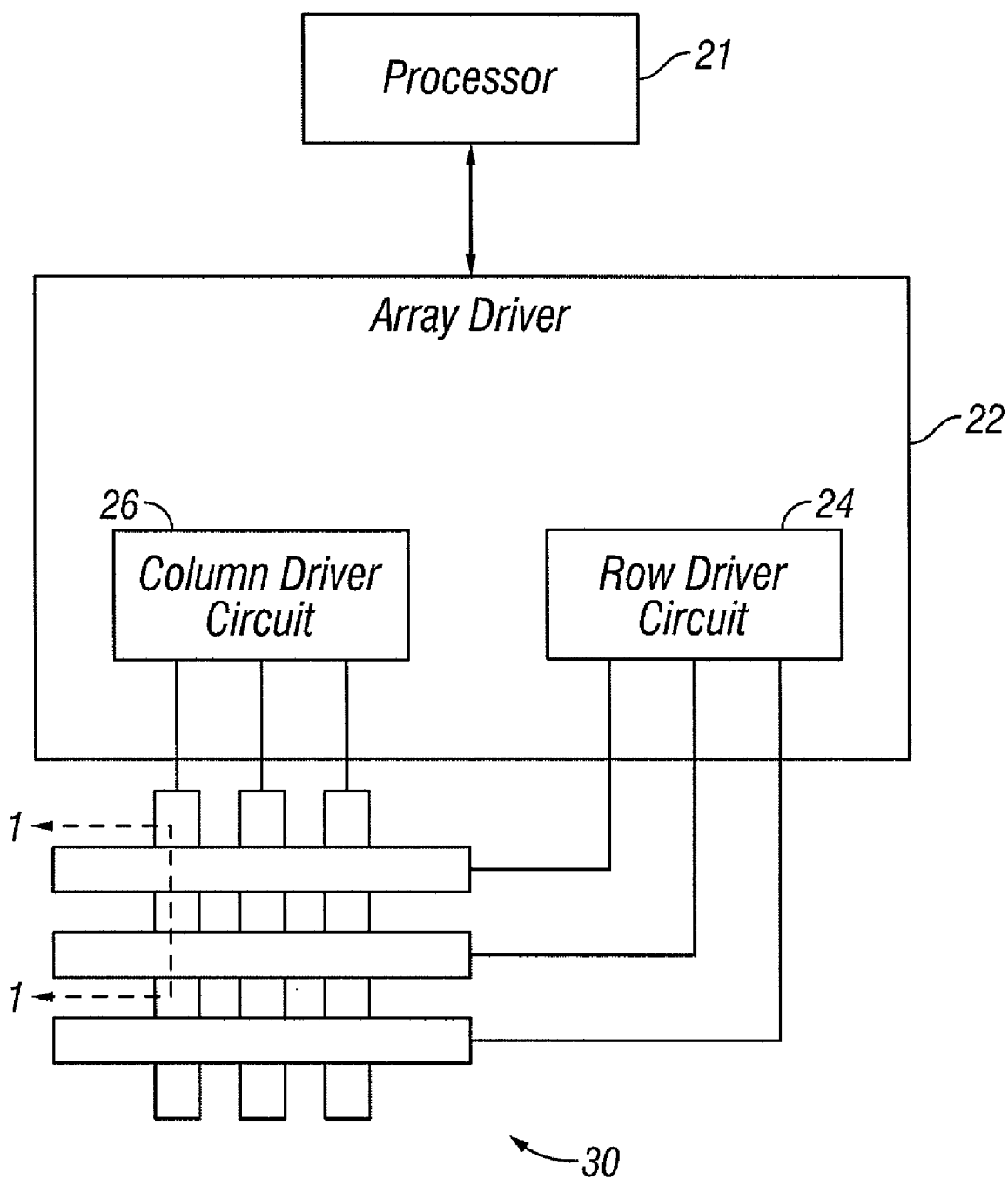
FIG. 2 is a system block diagram illustrating one embodiment of an electronic device incorporating a 3×3 interferometric modulator display.

FIG. 2 is a system block diagram illustrating one embodiment of an electronic device that may incorporate aspects of the invention. In the exemplary embodiment, the electronic device includes a processor 21 which may be any general purpose single- or multi-chip microprocessor such as an ARM, Pentium®, Pentium II®, Pentium III®, Pentium IV®, Pentium® Pro, an 8051, a MIPS®, a Power PC®, an ALPHA®, or any special purpose microprocessor such as a digital signal processor, microcontroller, or a programmable gate array. As is conventional in the art, the processor 21 may be configured to execute one or more software modules. In addition to executing an operating system, the processor may be configured to execute one or more software applications, including a web browser, a telephone application, an email program, or any other software application.

In one embodiment, the processor 21 is also configured to communicate with an array driver 22. In one embodiment, the array driver 22 includes a row driver circuit 24 and a column driver circuit 26 that provide signals to a display array or panel 30. The cross section of the array illustrated in FIG. 1 is shown by the lines 1-1 in FIG. 2. For MEMS interferometric modulators, the row/column actuation protocol may take advantage of a hysteresis property of these devices illustrated in FIG. 3. It may require, for example, a 10 volt potential difference to cause a movable layer to deform from the relaxed state to the actuated state. However, when the voltage is reduced from that value, the movable layer maintains its state as the voltage drops back below 10 volts. In the exemplary embodiment of FIG. 3, the movable layer does not relax completely until the voltage drops below 2 volts. Thus, there exists a window of applied voltage, about 3 to 7 V in the example illustrated in FIG. 3, within which the device is stable in either the relaxed or actuated state. This is referred to herein as the "hysteresis window" or "stability window." For a display array having the hysteresis characteristics of FIG. 3, the row/column actuation protocol can be designed such that during row strobing, pixels in the strobed row that are to be actuated are exposed to a voltage difference of about 10 volts, and pixels that are to be relaxed are exposed to a voltage difference of close to zero volts. After the strobe, the pixels are exposed to a steady state voltage difference of about 5 volts such that they remain in whatever state the row strobe put them in. After being written, each pixel sees a potential difference within the "stability window" of 3-7 volts in this example. This feature makes the pixel design illustrated in FIG. 1 stable under the same applied voltage conditions in either an actuated or relaxed pre-existing state. Since each pixel of the interferometric modulator, whether in the actuated or relaxed state, is essentially a capacitor formed by the fixed and moving reflective layers, this stable state can be held at a voltage within the hysteresis window with almost no power dissipation. Essentially no current flows into the pixel if the applied potential is fixed.

In typical applications, a display frame may be created by asserting the set of column electrodes in accordance with the desired set of actuated pixels in the first row. A row pulse is then applied to the row 1 electrode, actuating the pixels corresponding to the asserted column lines. The asserted set of column electrodes is then changed to correspond to the desired set of actuated pixels in the second row. A pulse is then applied to the row 2 electrode, actuating the appropriate pixels in row 2 in accordance with the asserted column electrodes. The row 1 pixels are unaffected by the row 2 pulse, and remain in the state they were set to during the row 1 pulse. This may be repeated for the entire series of rows in a sequential fashion to produce the frame. Generally, the frames are refreshed and/or updated with new display data by continually repeating this process at some desired number of frames per second. A wide variety of protocols for driving row and column electrodes of pixel arrays to produce display frames are also well known and may be used in conjunction with the present invention.

Figures 3, 4:
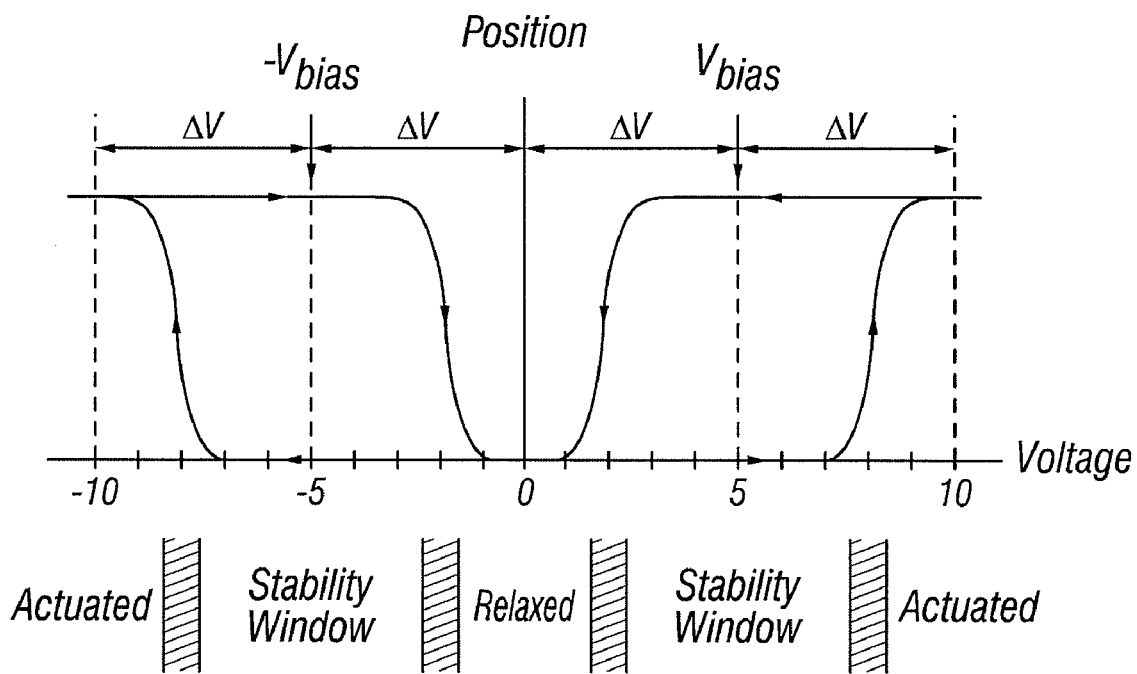
FIG. 3 is a diagram of movable mirror position versus applied voltage for one exemplary embodiment of an interferometric modulator of FIG. 1.
FIG. 4 is an illustration of a set of row and column voltages that may be used to drive an interferometric modulator display.
Figure 5A:
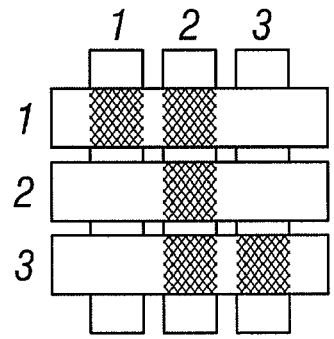
FIG. 5A illustrates one exemplary frame of display data in the 3×3 interferometric modulator display of FIG. 2.
Figure 5B:
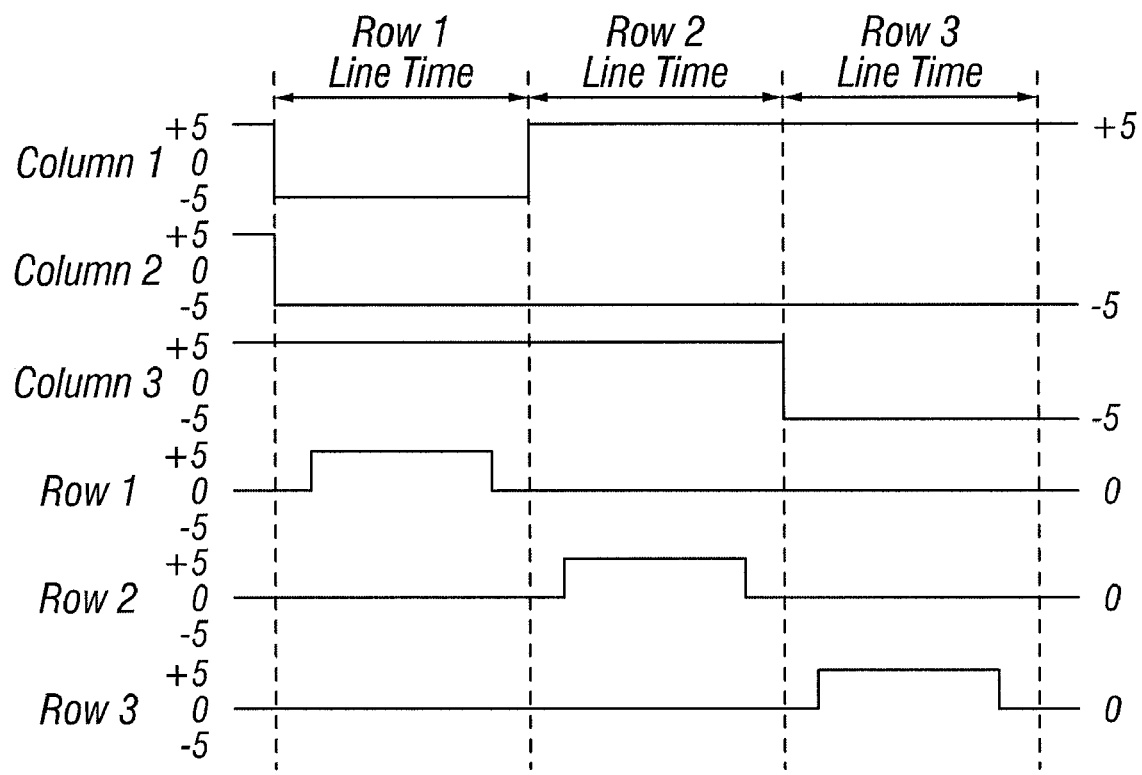
FIG. 5B illustrates one exemplary timing diagram for row and column signals that may be used to write the frame of FIG. 5A.

FIGS. 4, 5A, and 5B illustrate one possible actuation protocol for creating a display frame on the 3×3 array of FIG. 2. FIG. 4 illustrates a possible set of column and row voltage levels that may be used for pixels exhibiting the hysteresis curves of FIG. 3. In the FIG. 4 embodiment, actuating a pixel involves setting the appropriate column to $-V_{bias}$, and the appropriate row to $+\Delta V$, which may correspond to −5 volts and +5 volts, respectively. Relaxing the pixel is accomplished by setting the appropriate column to $+V_{bias}$, and the appropriate row to the same $+\Delta V$, producing a zero volt potential difference across the pixel. In those rows where the row voltage is held at zero volts, the pixels are stable in whatever state they were originally in, regardless of whether the column is at $+V_{bias}$, or $-V_{bias}$. As is also illustrated in FIG. 4, it will be appreciated that voltages of opposite polarity than those described above can be used, e.g., actuating a pixel can involve setting the appropriate column to $+V_{bias}$, and the appropriate row to $-\Delta V$. In this embodiment, releasing the pixel is accomplished by setting the appropriate column to $-V_{bias}$, and the appropriate row to the same $-\Delta V$, producing a zero volt potential difference across the pixel.

FIG. 5B is a timing diagram showing a series of row and column signals applied to the 3×3 array of FIG. 2 which will result in the display arrangement illustrated in FIG. 5A, where actuated pixels are non-reflective. Prior to writing the frame illustrated in FIG. 5A, the pixels can be in any state, and in this example, all the rows are at 0 volts, and all the columns are at +5 volts. With these applied voltages, all pixels are stable in their existing actuated or relaxed states.

In the FIG. 5A frame, pixels (1,1), (1,2), (2,2), (3,2) and (3,3) are actuated. To accomplish this, during a "line time" for row 1, columns 1 and 2 are set to −5 volts, and column 3 is set to +5 volts. This does not change the state of any pixels, because all the pixels remain in the 3-7 volt stability window. Row 1 is then strobed with a pulse that goes from 0, up to 5 volts, and back to zero. This actuates the (1,1) and (1,2) pixels and relaxes the (1,3) pixel. No other pixels in the array are affected. To set row 2 as desired, column 2 is set to −5 volts, and columns 1 and 3 are set to +5 volts. The same strobe applied to row 2 will then actuate pixel (2,2) and relax pixels (2,1) and (2,3). Again, no other pixels of the array are affected. Row 3 is similarly set by setting columns 2 and 3 to −5 volts, and column 1 to +5 volts. The row 3 strobe sets the row 3 pixels as shown in FIG. 5A. After writing the frame, the row potentials are zero, and the column potentials can remain at either +5 or −5 volts, and the display is then stable in the arrangement of FIG. 5A. It will be appreciated that the same procedure can be employed for arrays of dozens or hundreds of rows and columns. It will also be appreciated that the timing, sequence, and levels of voltages used to perform row and column actuation can be varied widely within the general principles outlined above, and the above example is exemplary only, and any actuation voltage method can be used with the systems and methods described herein.

Figure 6A:
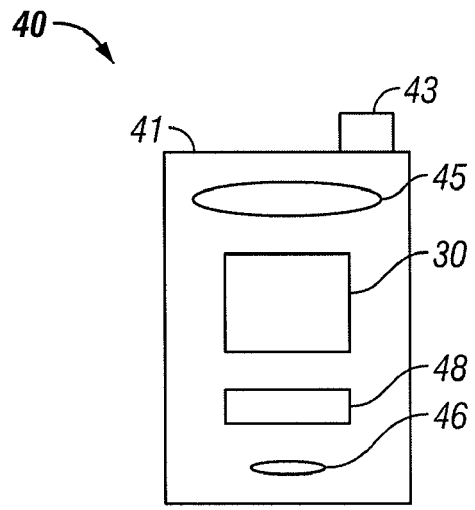
FIGS. 6A and 6B are system block diagrams illustrating an embodiment of a visual display device comprising a plurality of interferometric modulators.
Figure 6B:
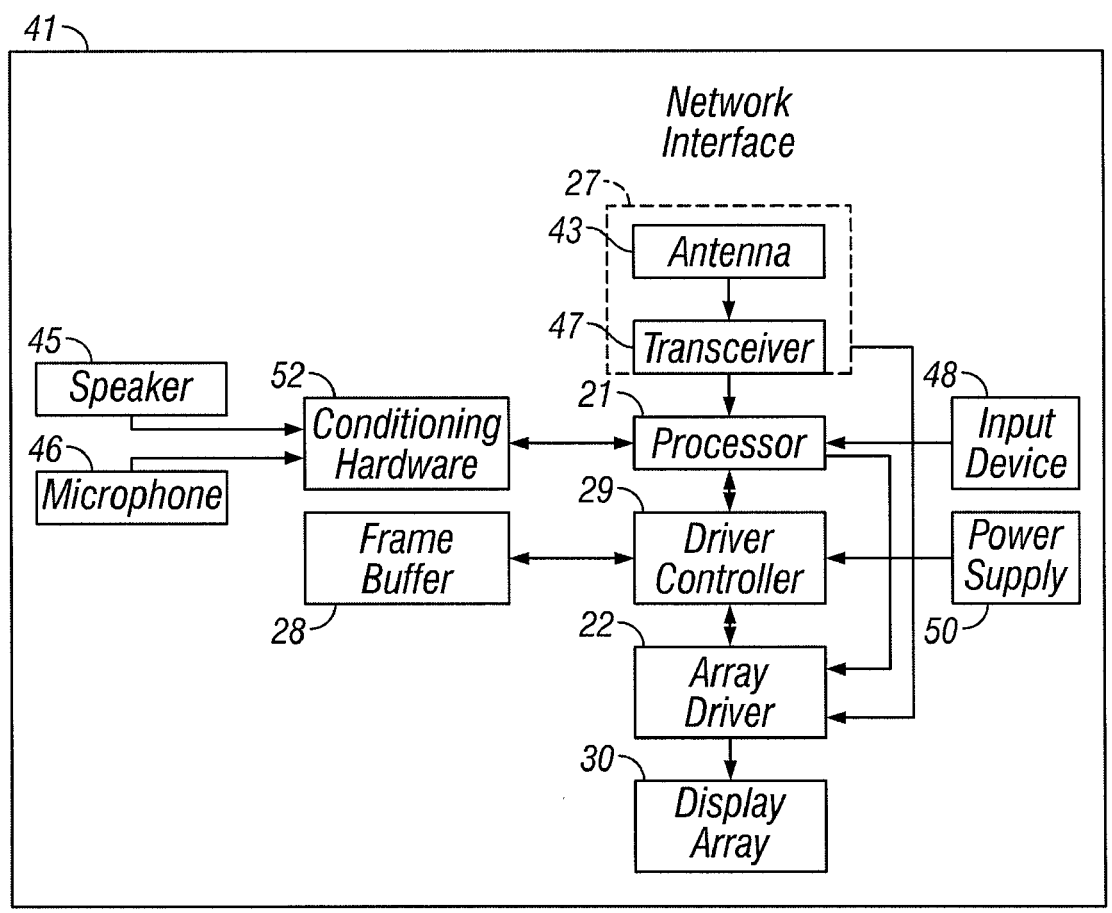

FIGS. 6A and 6B are system block diagrams illustrating an embodiment of a display device 40. The display device 40 can be, for example, a cellular or mobile telephone. However, the same components of display device 40 or slight variations thereof are also illustrative of various types of display devices such as televisions and portable media players.

The display device 40 includes a housing 41, a display 30, an antenna 43, a speaker 45, an input device 48, and a microphone 46. The housing 41 is generally formed from any of a variety of manufacturing processes as are well known to those of skill in the art, including injection molding and vacuum forming. In addition, the housing 41 may be made from any of a variety of materials, including, but not limited to, plastic, metal, glass, rubber, and ceramic, or a combination thereof. In one embodiment, the housing 41 includes removable portions (not shown) that may be interchanged with other removable portions of different color, or containing different logos, pictures, or symbols.

The display 30 of exemplary display device 40 may be any of a variety of displays, including a bi-stable display, as described herein. In other embodiments, the display 30 includes a flat-panel display, such as plasma, EL, OLED, STN LCD, or TFT LCD as described above, or a non-flat-panel display, such as a CRT or other tube device, as is well known to those of skill in the art. However, for purposes of describing the present embodiment, the display 30 includes an interferometric modulator display, as described herein.

The components of one embodiment of exemplary display device 40 are schematically illustrated in FIG. 6B. The illustrated exemplary display device 40 includes a housing 41 and can include additional components at least partially enclosed therein. For example, in one embodiment, the exemplary display device 40 includes a network interface 27 that includes an antenna 43, which is coupled to a transceiver 47. The transceiver 47 is connected to a processor 21, which is connected to conditioning hardware 52. The conditioning hardware 52 may be configured to condition a signal (e.g., filter a signal). The conditioning hardware 52 is connected to a speaker 45 and a microphone 46. The processor 21 is also connected to an input device 48 and a driver controller 29. The driver controller 29 is coupled to a frame buffer 28 and to an array driver 22, which in turn is coupled to a display array 30. A power supply 50 provides power to all components as required by the particular exemplary display device 40 design.

The network interface 27 includes the antenna 43 and the transceiver 47 so that the exemplary display device 40 can communicate with one or more devices over a network. In one embodiment, the network interface 27 may also have some processing capabilities to relieve requirements of the processor 21. The antenna 43 is any antenna known to those of skill in the art for transmitting and receiving signals. In one embodiment, the antenna transmits and receives RF signals according to the IEEE 802.11 standard, including IEEE 802.11(a), (b), or (g). In another embodiment, the antenna transmits and receives RF signals according to the BLUETOOTH standard. In the case of a cellular telephone, the antenna is designed to receive CDMA, GSM, AMPS, or other known signals that are used to communicate within a wireless cell phone network. The transceiver 47 pre-processes the signals received from the antenna 43 so that they may be received by and further manipulated by the processor 21. The transceiver 47 also processes signals received from the processor 21 so that they may be transmitted from the exemplary display device 40 via the antenna 43.

In an alternative embodiment, the transceiver 47 can be replaced by a receiver. In yet another alternative embodiment, network interface 27 can be replaced by an image source, which can store or generate image data to be sent to the processor 21. For example, the image source can be a digital video disc (DVD) or a hard-disc drive that contains image data, or a software module that generates image data.

Processor 21 generally controls the overall operation of the exemplary display device 40. The processor 21 receives data, such as compressed image data from the network interface 27 or an image source, and processes the data into raw image data or into a format that is readily processed into raw image data. The processor 21 then sends the processed data to the driver controller 29 or to frame buffer 28 for storage. Raw data typically refers to the information that identifies the image characteristics at each location within an image. For example, such image characteristics can include color, saturation, and gray-scale level.

In one embodiment, the processor 21 includes a microcontroller, CPU, or logic unit to control operation of the exemplary display device 40. Conditioning hardware 52 generally includes amplifiers and filters for transmitting signals to the speaker 45, and for receiving signals from the microphone 46. Conditioning hardware 52 may be discrete components within the exemplary display device 40, or may be incorporated within the processor 21 or other components.

The driver controller 29 takes the raw image data generated by the processor 21 either directly from the processor 21 or from the frame buffer 28 and reformats the raw image data appropriately for high speed transmission to the array driver 22. Specifically, the driver controller 29 reformats the raw image data into a data flow having a raster-like format, such that it has a time order suitable for scanning across the display array 30. Then the driver controller 29 sends the formatted information to the array driver 22. Although a driver controller 29, such as a LCD controller, is often associated with the system processor 21 as a stand-alone Integrated Circuit (IC), such controllers may be implemented in many ways. They may be embedded in the processor 21 as hardware, embedded in the processor 21 as software, or fully integrated in hardware with the array driver 22.

Typically, the array driver 22 receives the formatted information from the driver controller 29 and reformats the video data into a parallel set of waveforms that are applied many times per second to the hundreds and sometimes thousands of leads coming from the display's x-y matrix of pixels.

In one embodiment, the driver controller 29, array driver 22, and display array 30 are appropriate for any of the types of displays described herein. For example, in one embodiment, driver controller 29 is a conventional display controller or a bi-stable display controller (e.g., an interferometric modulator controller). In another embodiment, array driver 22 is a conventional driver or a bi-stable display driver (e.g., an interferometric modulator display). In one embodiment, a driver controller 29 is integrated with the array driver 22. Such an embodiment is common in highly integrated systems such as cellular phones, watches, and other small area displays. In yet another embodiment, display array 30 is a typical display array or a bi-stable display array (e.g., a display including an array of interferometric modulators).

The input device 48 allows a user to control the operation of the exemplary display device 40. In one embodiment, input device 48 includes a keypad, such as a QWERTY keyboard or a telephone keypad, a button, a switch, a touch-sensitive screen, or a pressure- or heat-sensitive membrane. In one embodiment, the microphone 46 is an input device for the exemplary display device 40. When the microphone 46 is used to input data to the device, voice commands may be provided by a user for controlling operations of the exemplary display device 40.

Power supply 50 can include a variety of energy storage devices as are well known in the art. For example, in one embodiment, power supply 50 is a rechargeable battery, such as a nickel-cadmium battery or a lithium ion battery. In another embodiment, power supply 50 is a renewable energy source, a capacitor, or a solar cell including a plastic solar cell, and solar-cell paint. In another embodiment, power supply 50 is configured to receive power from a wall outlet.

In some embodiments, control programmability resides, as described above, in a driver controller which can be located in several places in the electronic display system. In some embodiments, control programmability resides in the array driver 22. Those of skill in the art will recognize that the above-described optimizations may be implemented in any number of hardware and/or software components and in various configurations.

Figure 7A:
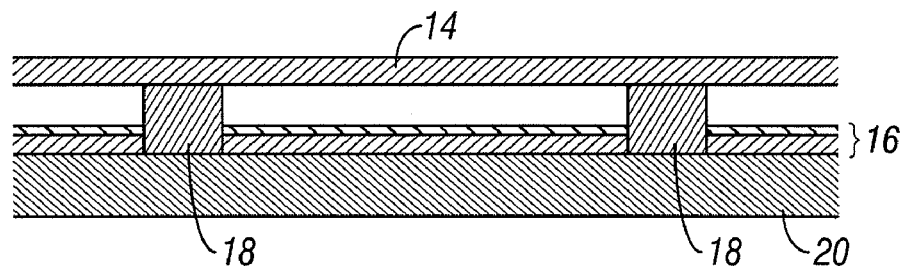
FIG. 7A is a cross section of the device of FIG. 1.
Figure 7B:
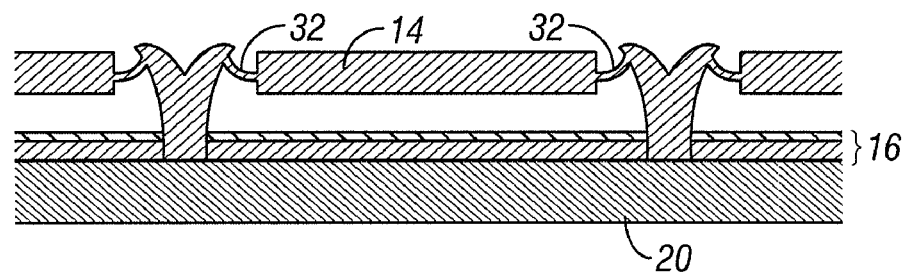
FIG. 7B is a cross section of an alternative embodiment of an interferometric modulator.
Figure 7C:
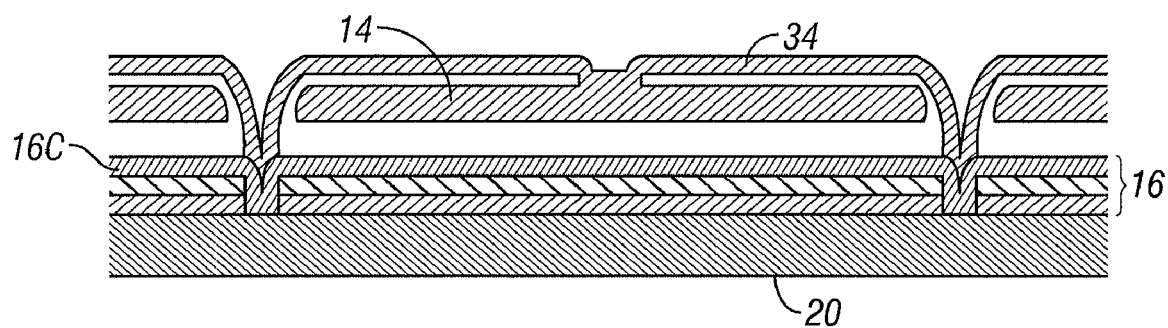
FIG. 7C is a cross section of another alternative embodiment of an interferometric modulator.
Figure 7D:
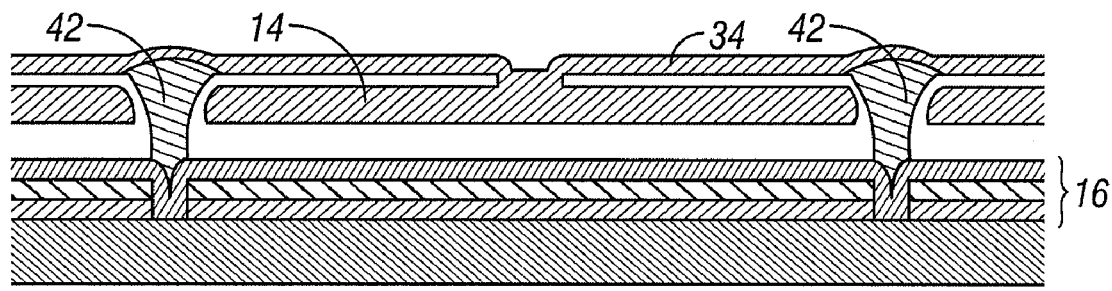
FIG. 7D is a cross section of yet another alternative embodiment of an interferometric modulator.
Figure 7E:
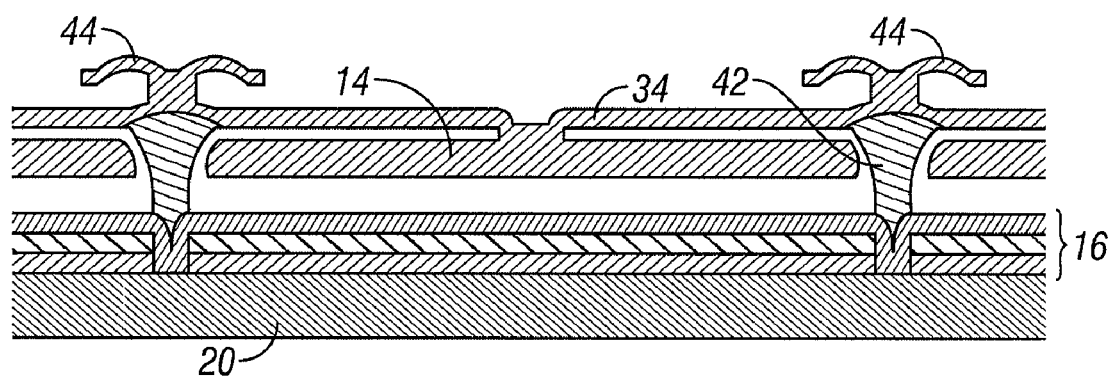
FIG. 7E is a cross section of an additional alternative embodiment of an interferometric modulator.

The details of the structure of interferometric modulators that operate in accordance with the principles set forth above may vary widely. For example, FIGS. 7A-7E illustrate five different embodiments of the movable reflective layer 14 and its supporting structures. FIG. 7A is a cross section of the embodiment of FIG. 1, where a strip of metal material 14 is deposited on orthogonally extending supports 18. In FIG. 7B, the moveable reflective layer 14 is attached to supports at the corners only, on tethers 32. In FIG. 7C, the moveable reflective layer 14 is suspended from a deformable layer 34, which may comprise a flexible metal. The deformable layer 34 connects, directly or indirectly, to the substrate 20 around the perimeter of the deformable layer 34. These connections are herein referred to as support posts. The embodiment illustrated in FIG. 7D has support post plugs 42 upon which the deformable layer 34 rests. The movable reflective layer 14 remains suspended over the gap, as in FIGS. 7A-7C, but the deformable layer 34 does not form the support posts by filling holes between the deformable layer 34 and the optical stack 16. Rather, the support posts are formed of a planarization material, which is used to form support post plugs 42. The embodiment illustrated in FIG. 7E is based on the embodiment shown in FIG. 7D, but may also be adapted to work with any of the embodiments illustrated in FIGS. 7A-7C, as well as additional embodiments not shown. In the embodiment shown in FIG. 7E, an extra layer of metal or other conductive material has been used to form a bus structure 44. This allows signal routing along the back of the interferometric modulators, eliminating a number of electrodes that may otherwise have had to be formed on the substrate 20.

In embodiments such as those shown in FIG. 7, the interferometric modulators function as direct-view devices, in which images are viewed from the front side of the transparent substrate 20, the side opposite to that upon which the modulator is arranged. In these embodiments, the reflective layer 14 optically shields the portions of the interferometric modulator on the side of the reflective layer opposite the substrate 20, including the deformable layer 34. This allows the shielded areas to be configured and operated upon without negatively affecting the image quality. Such shielding allows the bus structure 44 in FIG. 7E, which provides the ability to separate the optical properties of the modulator from the electromechanical properties of the modulator, such as addressing and the movements that result from that addressing. This separable modulator architecture allows the structural design and materials used for the electromechanical aspects and the optical aspects of the modulator to be selected and to function independently of each other. Moreover, the embodiments shown in FIGS. 7C-7E have additional benefits deriving from the decoupling of the optical properties of the reflective layer 14 from its mechanical properties, which are carried out by the deformable layer 34. This allows the structural design and materials used for the reflective layer 14 to be optimized with respect to the optical properties, and the structural design and materials used for the deformable layer 34 to be optimized with respect to desired mechanical properties.

In certain MEMS devices, such as interferometric modulators of the types described above, the large surface area to gap ratios and high surface energies create conditions highly favorable to adhesion, due at least in part to Van der Waals and capillary forces. Depending on the particular configuration of the device and depending on the environmental conditions, the adhesion forces can surpass the mechanical restoring force of the movable layer, resulting in permanent, non-recoverable adhesion when the movable layer contacts the opposing surface. In general, permanent adhesion or "stiction" in a MEMS device is undesirable trait. However, it is possible to form MEMS structures configured to collapse and achieve stiction when exposed to a specific environmental condition or set of conditions.

By employing interferometric modulators in these structures, it is possible to design passive sensor devices capable of indicating to a human observer, without the need for external sensing electronics, whether they have been exposed to the specified environmental condition or set of conditions. By configuring such a device so as to ensure permanent stiction upon collapse—that is, so as to prevent spontaneous restoration to an original, uncollapsed state—such a device may be used to indicate even a one-time exposure to the specified environmental condition or set of conditions, regardless of any later change in the environment. In addition, the delicate nature of the films used in interferometric modulators makes intentional alteration of the sensor display impossible without destroying the sensor device permanently. This type of sensor is thus ideal for use in consumer applications which are sensitive to environmental conditions, such as food products (e.g. milk, eggs, wine) and medical products (e.g. blood, plasma, vaccines) which can degrade in certain environmental conditions, or applications involving sports activities (e.g. scuba diving, flying, mountain climbing) or work-related activities (e.g. welding, mining) where exposure to certain environmental conditions must be monitored. The ease of use of these devices makes them ideal when unambiguous identification of changes in environmental conditions have exceeded a predefined threshold. Such devices can also be used in multiples and can be configured with varying optical responses to create text, graphic, or color-based sensor displays.

Embodiments of the invention generally include a movable member designed to deform or otherwise collapse and achieve contact with an opposing surface in response to being exposed to a particular environmental condition, such as, for example, a particular temperature or humidity threshold, a particular chemical species or concentration thereof, a particular level or type of radiation, a particular level of mechanical shock, or a combination of these or other environmental conditions. Embodiments may also be configured to ensure that, once collapsed, adhesion forces will exceed any mechanical restoring force required to restore the movable member to its original undeformed or uncollapsed state. In certain embodiments, the movable member may be provided with a package configured to seal an internal environment of the sensor from the external environment and thus protect the device in storage until the user exposes it to the environment that is to be sensed. The sealed internal environment can be configured to ensure that, if the movable member does collapse before the package is opened, such collapse will not be permanent. These and other embodiments can thus be activated by an end user upon opening of the package. Alternative embodiments can include a sealed internal environment configured with, for example, a selected high level of humidity, so as to ensure that permanent stiction will occur upon collapse.

Chemical/Humidity/Temperature Sensor

Figure 8A:
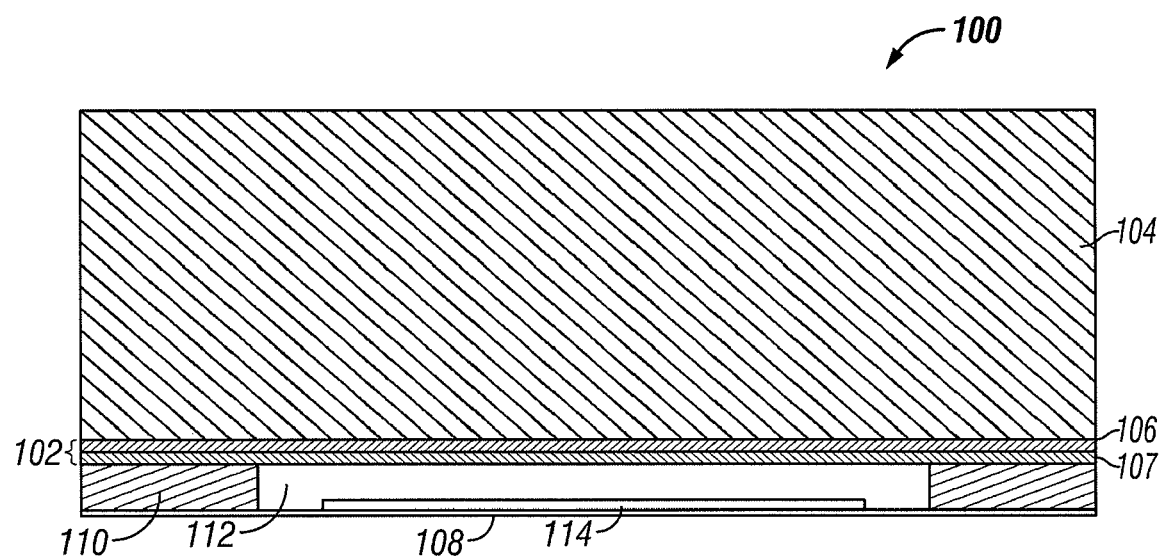
FIG. 8A is a cross-section of a sensor according to an embodiment, shown in an unactuated state.
Figure 8B:
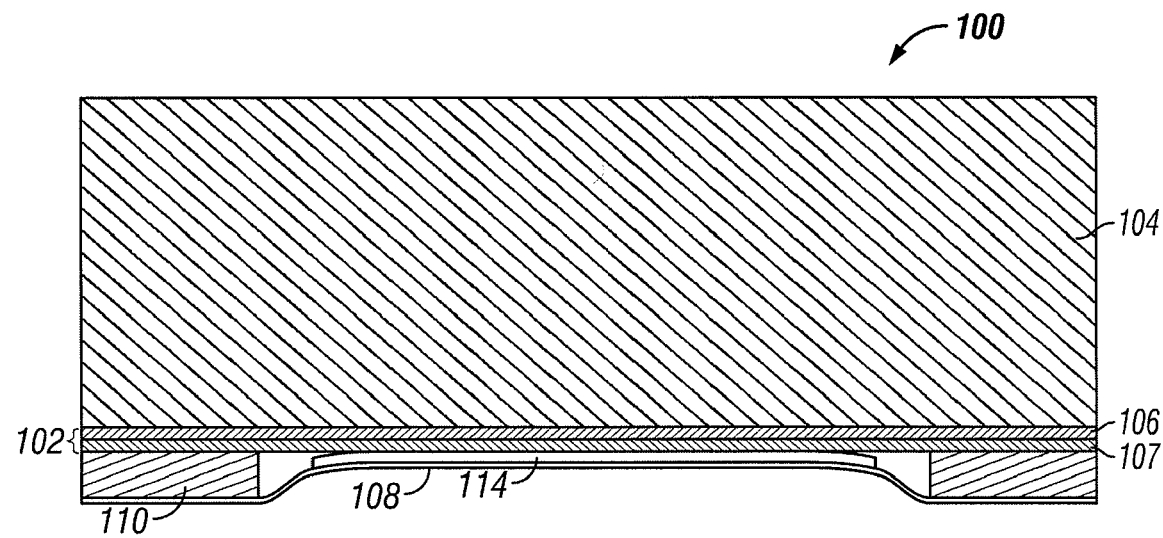
FIG. 8B is a cross-section of a sensor according to the embodiment of FIG. 8A, shown in an actuated (collapsed) state.

FIGS. 8A and 8B illustrate an environmental sensor 100 according to one embodiment of the invention. The sensor 100 comprises an optical stack 102 formed on a transmissive substrate 104, where the optical stack 102 includes a partially reflective layer 106 and an electrically insulating layer 107. The sensor 100 further comprises a movable member 108 spaced apart from the optical stack 102 by one or more posts 110 to define a gap 112. In embodiments in which the movable member 108 comprises a reflective layer, the space between 106 and 108 functions as an interferometric cavity. An observer viewing the sensor 100 through the transmissive substrate 104 will thus be able to easily observe a change in the position of the movable member 108 relative to the optical stack 102, as the light reflected by the sensor 100 is dependent on the height of the interferometric gap 112.

As shown in FIG. 8A, the movable member 108 includes an expansion layer 114 disposed on the side of the movable member 108 facing the optical stack 102. The expansion layer 114 can be configured to expand in volume when exposed to a specific environmental condition occurring within the gap 112, such as, for example, moisture, a particular level of acidity or alkalinity, or the presence of a particular chemical species. The expansion layer 114 can further be configured to expand by an amount sufficient to induce bending in the movable member 108 such that the movable member 108 (and/or the expansion layer 114) comes into contact with the optical stack 102. FIG. 8B shows the sensor 100 of FIG. 8A in a collapsed state, the sensor having been exposed to the selected environmental condition.

The expansion layer 114 can comprise one or more of several materials exhibiting the desired properties for the particular application, such as, for example, cross-linked polyethylene oxide (a moisture absorber) or hydrogels. In alternative embodiments, a contraction layer can be disposed on the opposite side of the membrane. The contraction layer can be configured to contract when exposed to a specific environmental condition by an amount sufficient to induce bending in the movable member 108 such that the movable member 108 comes into contact with the optical stack 102. Such a contraction layer may comprise, for example, a hygroscopic aerogel. The expansion or contraction layer can also comprise a polymeric material such as thin poly (hydroxyethyl methacrylate) (PHEMA) or poly (methyl methacrylate) (PMMA), which will expand when exposed to alcohols (methanol, isopropanol) as well as water vapor. A mechanochemically responsive polymeric film can also be used which expands or contracts in response to its ambient chemical environment. Another example of a suitable material is RTV silicone rubber, which can be configured to expand when exposed to a particular chemical analyte and contract when the analyte is removed. An expansion (or contraction) layer as described herein can be formed by, for example, applying the layer to the movable member 108 prior to its deposition.

Additionally or alternatively, embodiments can be configured to react in a specified way in response to temperature. Changes in temperature can induce strong variations in the as-deposited stress of micro-mechanical thin film structures, resulting in deflection of the thin film structure with respect to the substrate. Where the deflection response is known, the movable member 108 can thus be configured to deflect when exposed to a given temperature threshold by an amount sufficient to create contact with the opposing surface of the optical stack 102. In alternative embodiments, the movable member 108 can comprise two or more films having different coefficients of thermal expansion, selected to induce deformation of the movable member sufficient to cause contact with the optical stack in response to exposure to a given temperature. The movable member 108 can also be tethered or otherwise attached to a rigid substrate, and configured with a coefficient of thermal expansion selected to induce deformation or sagging sufficient to induce to cause contact with the optical stack in response to exposure to a given temperature.

In these and other embodiments, the movable member 108 and/or the optical stack 102 can be specially formed or treated so as to ensure that permanent stiction will occur when the movable member 108 contacts the optical stack 102. Embodiments are thus configured to prevent the movable member 108 from restoring itself to its original position after making contact with the optical stack 102, even when the temperature or humidity returns to normal or the deforming agent is no longer present. Embodiments can thus be tunable to indicate exposure to a wide range of sensitivities. A humidity sensor, for example, can be tuned to indicate exposure from 10% humidity or less, up to 90% humidity or more.

The tendency to adhere can be enhanced in a number of ways; for example, by driving charge into the surface dielectric film of the optical stack, thereby increasing electrostatic force upon contact, by utilizing dissimilar contact materials with greater mutual surface attraction, by roughening one or both of the contact surfaces, by coating one or both of the contact surfaces with an adhesive, or by increasing the size of the contact area between the two surfaces. In embodiments comprising an expansion layer disposed on the stack-facing surface of the movable member, the expansion layer may come into contact with the optical stack when the membrane deforms. Accordingly, the thickness and surface properties of the expansion layer material will influence adhesion between the surfaces. Where required, the tendency to adhere can be reduced by fabricating the device with smooth contact surfaces (having an RMS roughness <1 nm, for example), by passivating the contact surfaces to reduce their surface energy, by coating them with self-assembled monolayers (SAMs) or atomic layer deposited (ALD) films, or by using similar contact materials (e.g. metal/metal, dielectric/dielectric) having less mutual attraction.

Adhesion can also be influenced by moisture levels. Embodiments can include a package sealed to the environment, for example with a known, low level of humidity, to ensure that permanent stiction will not occur until the sensor is activated by opening the package to the environment and exposing it to a level of humidity allowing for permanent stiction to occur. Humidity levels as low as 100 ppmv, for example, can lead to permanent, non-recoverable adhesion on contact. The humidity threshold to achieve permanent adhesion can be further tailored as described above; thus, embodiments can be configured to cover a wide range of sensitivities. Further, embodiments can be configured to sense and indicate exposure to a particular combination of multiple stimuli, such as temperature and humidity. Alternatively, some embodiments can comprise a package sealed with a pre-defined and stable operating state that is only influenced by specific stimuli, such as temperature or shock, that may be coupled through the package to induce collapse of the membrane. For example, embodiments can be sealed with a known, high concentration of moisture or particular chemicals, to ensure that stiction will be permanent when an external stimulus is transmitted through the package.

Shock Sensor

Figure 9A:
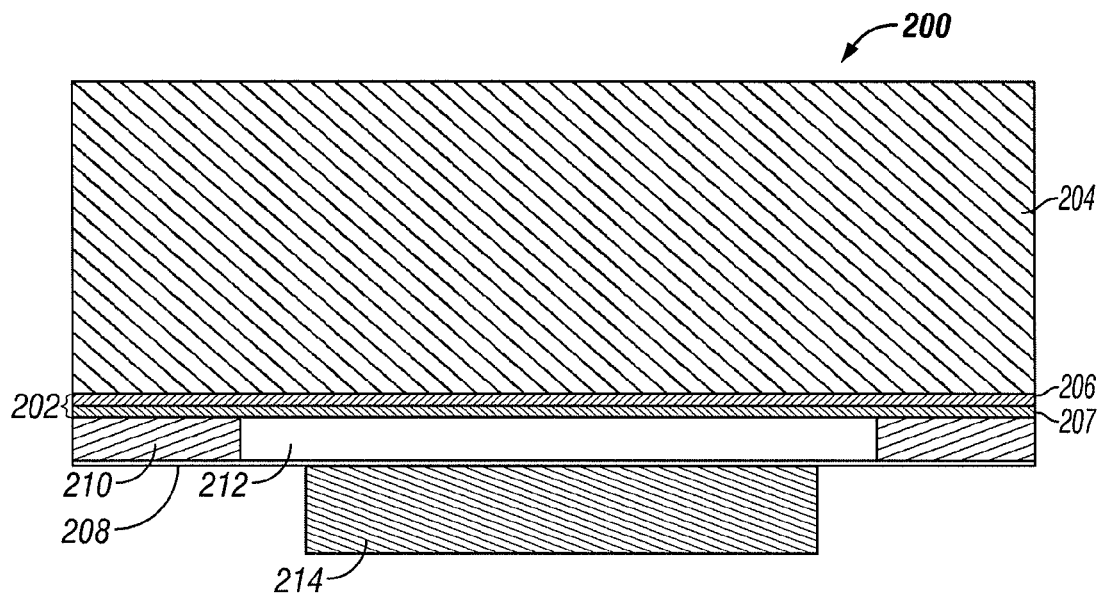
FIG. 9A is a cross-section of a sensor according to an alternative embodiment, shown in an unactuated state.
Figure 9B:
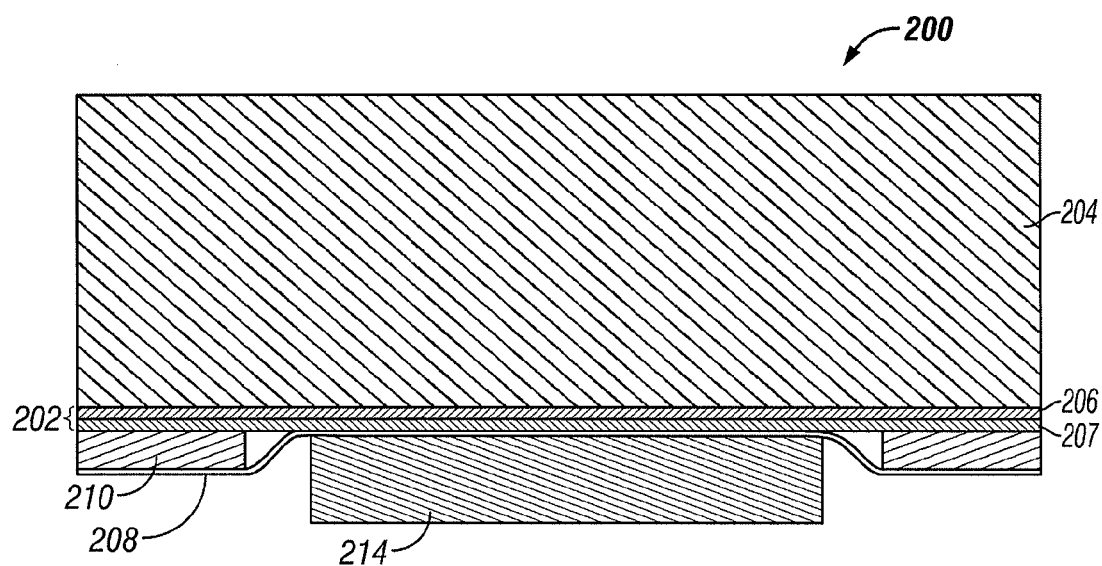
FIG. 9B is a cross-section of a sensor according to the embodiment of FIG. 9A, shown in an actuated (collapsed) state.

With reference now to FIGS. 9A and 9B, an environmental sensor 200 according to an alternative embodiment is illustrated. The sensor 200 comprises an optical stack 202 formed on a transmissive substrate 204, where the optical stack 202 includes a partially reflective layer 206 and an electrically insulating layer 207. The sensor 200 further comprises a movable member 208 spaced apart from the optical stack 202 by one or more posts 210 to define a gap 212. In embodiments in which the movable member 208 comprises a reflective layer, the space between 206 and 208 functions as an interferometric cavity. An observer viewing the sensor 200 through the transmissive substrate 204 will thus be able to easily observe a change in the position of the movable member 208 relative to the optical stack 202, as the light reflected by the sensor 200 is dependent on the height of the interferometric gap 212.

As shown in FIG. 9A, a proof mass 214 is disposed on a side of the movable member 208, such that a selected level of shock received in a direction generally normal to the surface of the movable member 208 will induce an acceleration of the proof mass 214 and force the movable member 208 into contact with the optical stack 202. For example, as illustrated by the calculation below, for a MEMS structure requiring an actuation force of an approximately 1 micro-newton ($\mu$N), a 10 $\mu$g proof mass will force the structure to collapse in response to a 10 g acceleration:

$$F = m \cdot a$$
$$m = \frac{F}{a}$$
$$m = \frac{1\,\mu\text{N}}{10 \cdot 9.8 \frac{m}{s^2}} \cong 10\,\mu\text{g}$$

The required volume for the proof mass can then be determined based on the density of the proof mass material as follows:

$$\rho = \frac{m}{V}$$
$$V = \frac{m}{\rho}$$
$$V = \frac{10\,\mu\text{g}}{8800 \frac{\text{kg}}{m^3}} \cong 1.2 \times 10^6\,\mu\text{m}^3$$

In some embodiments, the proof mass comprises a high-density material, such as nickel ($\rho \approx 8800$ kg/m$^3$). For a 10 g sensor as described above, a $1.2 \times 10^6$ $\mu$m$^3$ block of nickel (for example, having dimensions of 200 $\mu$m×200 $\mu$m×30 $\mu$m) can be used to induce collapse under a 10 g acceleration. In embodiments in which the movable member also comprises nickel, such a proof mass can be formed, for example, as follows: during fabrication of the MEMS device and before the movable member is removed from the sacrificial layer, the movable member can be masked so as to leave a 200 µm×200 µm area exposed. The substrate can then be placed in a nickel electroplating bath and additional nickel can be plated on the exposed area up to the desired thickness of 30 µm. Thus, the proof mass can comprise the same material as the movable member, and/or can be formed directly on the movable member. Alternatively, the proof mass can comprise a different material than the movable member, and/or can be adhered to the movable member, for example using an adhesive.

In other embodiments, the proof mass is manufactured on a separate, but similarly-sized substrate as the sensor. For example, a thick (15-30 µm) layer of gold can be deposited on a thin (~100-200 µm) silicon substrate, patterned, and then aligned and attached, using thermocompression bonding, to a movable membrane which is coated with sputtered gold (~1-3 µm). The thin silicon support can then be removed, for example by dissolving it in a KOH solution, before releasing the movable membrane.

FIG. 9B shows the sensor 200 of FIG. 9A in a collapsed state, the sensor having been exposed to the selected level of physical shock. In these and other embodiments, the movable member 208 and/or the optical stack 202 can be specially formed or treated, as described above in connection with FIGS. 8A-8B, so as to ensure that permanent stiction will occur when the movable member 208 contacts the optical stack 202. Embodiments are thus configured to prevent the movable member 208 from restoring itself to its original position after making contact with the optical stack 202, even after the physical shock has passed.

Radiation Sensor

Figure 10A:
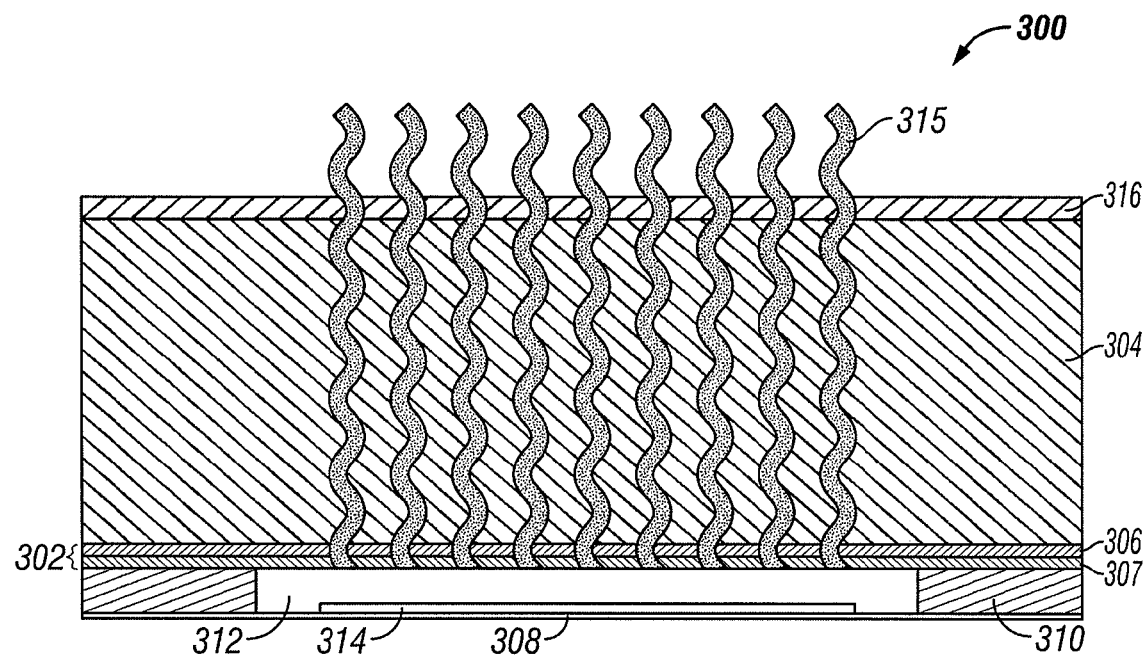
FIG. 10A is a cross-section of a sensor according to a further embodiment, shown in an unactuated state.
Figure 10B:
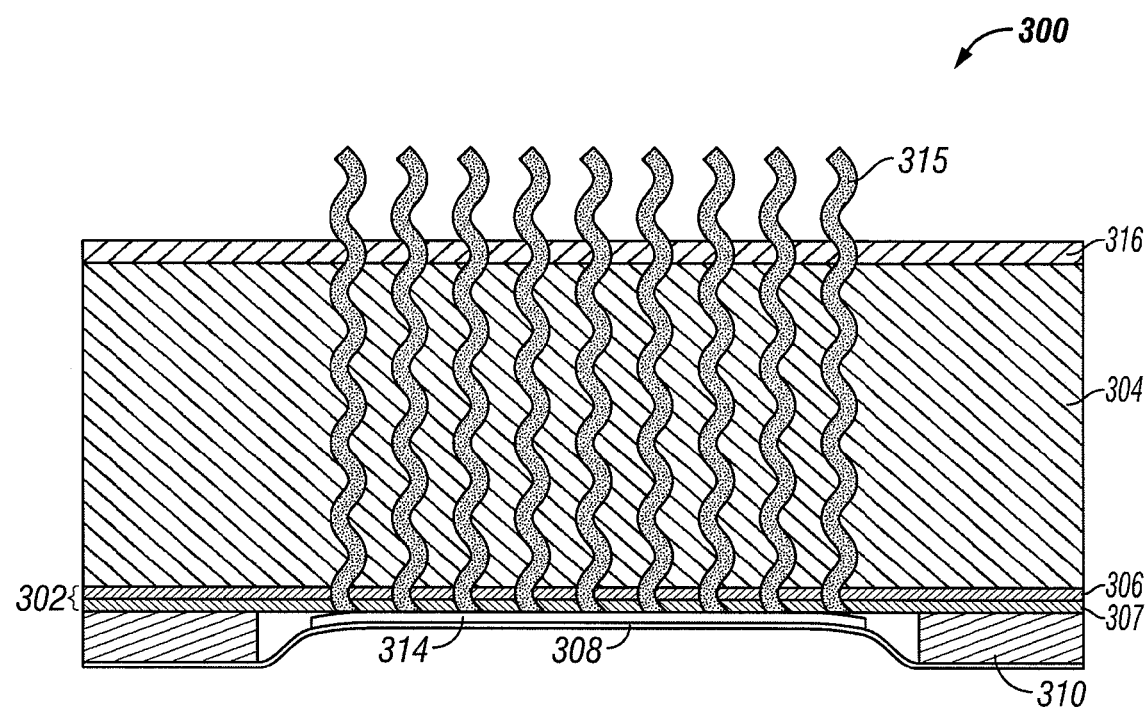
FIG. 10B is a cross-section of a sensor according to the embodiment of FIG. 10A, shown in an actuated (collapsed) state.

With reference now to FIGS. 10A and 10B, an environmental sensor 300 according to a further embodiment is illustrated. The sensor 300 comprises an optical stack 302 formed on a transmissive substrate 304, where the optical stack 302 includes a partially reflective layer 306 and an electrically insulating layer 307. The sensor 300 further comprises a movable member 308 spaced apart from the optical stack 302 by one or more posts 310 to define a gap 312. In embodiments in which the movable member 308 comprises a reflective layer, the space between 306 and 308 functions as an interferometric cavity. An observer viewing the sensor 300 through the transmissive substrate 304 will thus be able to easily observe a change in the position of the movable member 308 relative to the optical stack 302, as the light reflected by the sensor 300 is dependent on the height of the interferometric gap 312.

As shown in FIG. 10A, the movable member 308 comprises a radiation-sensitive layer or coating 314 disposed on the side of the movable member 308 facing the optical stack 302. The radiation-sensitive layer 314 can be configured to expand in volume when exposed to a particular type or level of radiation 315. The radiation-sensitive layer 314 can further be configured to expand by an amount sufficient to induce bending in the movable member 308 such that the movable member 308 (and/or the expansion layer 314) deflects across the gap 312 and comes into contact with the optical stack 302. FIG. 10B shows the sensor 300 of FIG. 10A in a collapsed state, the sensor having been exposed to the selected type or level of radiation.

The radiation-sensitive layer 314 can comprise, for example, an optically absorbing pigment such as carbon black, or a layer of chromium or indium tin oxide. Where the radiation-sensitive layer absorbs radiation and produces localized heating, such deformation can occur as a result of differential thermal expansion. Other embodiments can include a radiation-sensitive layer 314 designed to undergo a change in volume when exposed to radiation. Examples of such a material include polymer networks containing azobenzene liquid-crystalline (LC) moieties, which are capable of changing their macroscopic shape when exposed to light. Other polymer gels containing ionizable moieties, as well as certain inorganic materials such as vanadium dioxide, also display photosensitivity and can be incorporated into embodiments. In addition, several photosensitive polymeric materials exist which can be patterned lithographically into discrete "patches" within the boundary of each interferometric modulator to optimize their mechanical input to the movable member. One such material is PMMA, sold in a photoresist formulation commercially by MicroChem Corp, Newton, Mass. This material can be spin-coated up to relatively high thicknesses (up to 5 µm) in a standard clean room environment and subsequently patterned using deep UV illumination. It is also insensitive to the chemical etch of the release process used to remove the sacrificial layer and leave a suspended moveable member. By incorporating a radiation-sensitive coating 314 in a sensor 300 according to embodiments of the invention, such that permanent stiction will occur upon exposure of the sensor 300 to a predetermined type or level of radiation, a passive sensor is provided that directly displays a response to incident radiation without any additional components.

In certain embodiments, a polarizing coating or film 316 can be disposed on a side of the substrate 304 opposite the optical stack 302 to provide additional control of the direction of bending in the movable member 308. For example, in embodiments comprising a coating 314 comprising a polymer network as described above, the coating 314 may be directionally sensitive to incident radiation. The polarizing film 316 can thus be configured to promote a preferred mechanical response from the coating 314, and thus from the movable member 308, as shown in FIG. 10B.

In these and other embodiments, the movable member 308 and/or the optical stack 302 can be specially formed or treated, as described above in connection with FIGS. 8A-8B, so as to ensure that permanent stiction will occur when the movable member 308 contacts the optical stack 302. Embodiments are thus configured to prevent the movable member 308 from restoring itself to its original position after making contact with the optical stack 302, even after the deforming radiation is no longer present.

In another embodiment, an array of interferometric modulators with different stiction thresholds may be manufactured on a single substrate such that, for example, the highest level of humidity to which a device is exposed may be recorded. Continuing with the example, a user could determine that at some point in time since the device was activated it was exposed to a humidity level of 65%, but not more than 70%, based on some of the interferometric modulators reaching permanent stiction with others not having done so. As opposed to having a single threshold level, the maximum level may be recorded, for example with humidity, temperature (87 degrees but not 88 degrees), types of chemicals (exposure to carbon monoxide but not sulfur) or radiation (in degree or type—exposure to ultraviolet but not x-ray), force (exposure to 5 g but not 6 g), and so on.

Multiple-Stimuli Sensor

As mentioned earlier, embodiments can be configured to sense multiple stimuli simultaneously. Embodiments can be configured to sense any combination of energy inputs from the environment sufficient to induce a permanent change in the position of the movable member of the sensor.

For example, one embodiment can include a movable member comprising an expansion layer or contraction layer as described above, which is configured to cause a movable layer of the device to deform and cause the device to collapse when exposed to a particular level of acidity or alkalinity, or the presence of a particular chemical species. Such an embodiment can also be configured such that the collapse will only be permanent if it occurs at or above a particular temperature threshold. Additionally or alternatively, such an embodiment can be configured such that the collapse will only be permanent if it occurs at or above a particular humidity threshold.

Another embodiment can include a thin film stack configured with, for example, multiple layers having different coefficients of thermal expansion, as described above, so as to induce deformation and collapse of the movable member when the device is exposed to a predetermined temperature threshold. Such an embodiment can also be configured such that the collapse will only be permanent if it occurs at or above a particular humidity threshold.

A further embodiment can include a movable member comprising a radiation-sensitive layer as described above, which is configured to cause a movable layer of the device to deform and cause the device to collapse when exposed to a particular level or type of radiation. Such an embodiment can also be configured such that the collapse will only be permanent if it occurs at or above a particular temperature threshold. Additionally or alternatively, such an embodiment can be configured such that the collapse will only be permanent if it occurs at or above a particular humidity threshold.

A still further embodiment can include a proof mass as described above, which is configured to cause a movable layer of the device to deform and cause the device to collapse when exposed to a particular level of mechanical shock. Such an embodiment can be configured such that the collapse will only be permanent if it occurs at or above a particular temperature threshold. Additionally or alternatively, such an embodiment can be configured such that the collapse will only be permanent if it occurs at or above a particular humidity threshold.

Package

Figure 11:
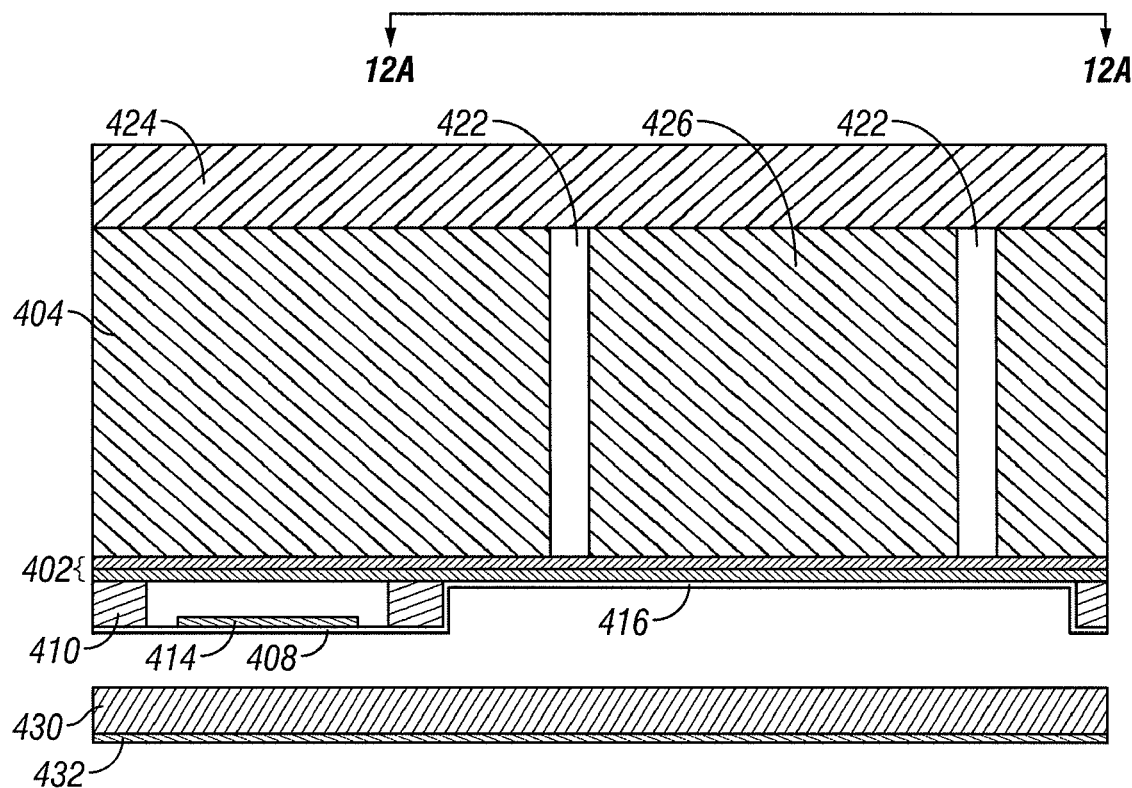
FIG. 11 is a cross-section view of a portion of a sensor having a sealing package according to an embodiment.
Figure 12A:
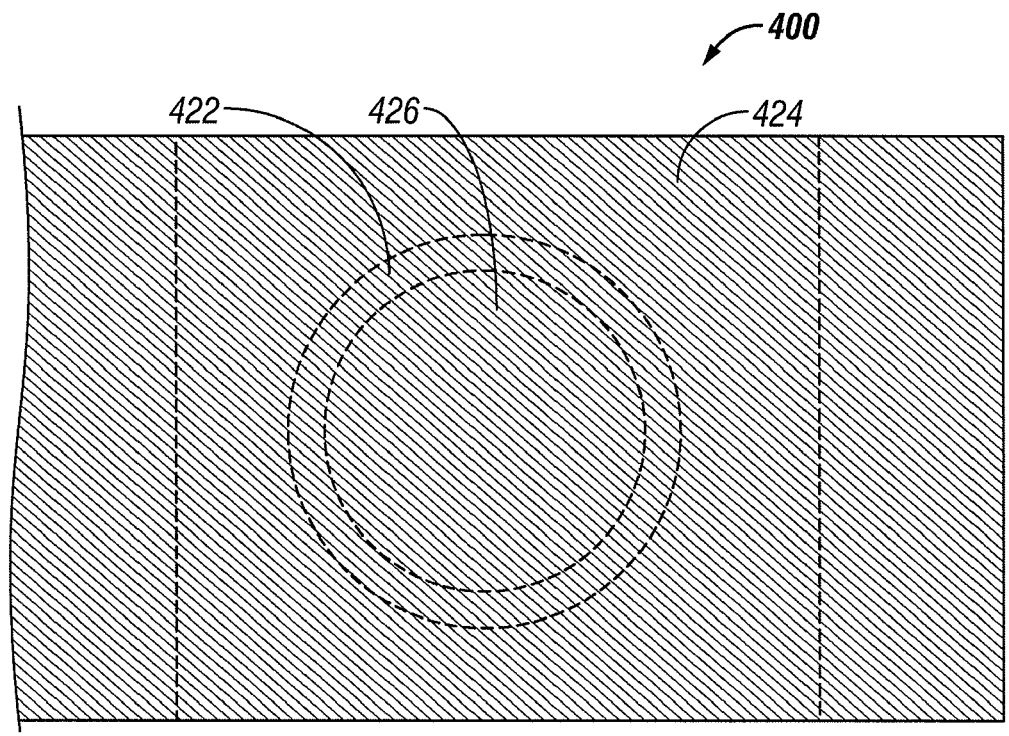
FIG. 12A is a partially cut away top view of the sensor of FIG. 11.

With reference now to FIGS. 11 and 12, an example of a sensor 400 according to another embodiment is described. The sensor 400 comprises an optical stack 402 formed on a transmissive substrate 404, through which the state of the sensor 400 may be viewed. The sensor 400 also includes a movable member 408 spaced apart from the optical stack 402 by one or more posts 410 to define a gap. The movable member 408 can include a reactive member 414, such as a chemical-reactive coating, a humidity, temperature, or radiation sensitive layer, or a proof mass configured to couple external shock, as described above. The sensor 400 can also include a protective layer 430 provided at or near the side of the movable member 408 facing away from the optical stack 402. The protective layer 430 can be configured to protect the active area of the sensor 400, especially the movable member 408, from the external environment until a user activates the sensor 400. To achieve desired conditions in the internal environment of the sensor 400, the protective layer 430 can be attached (that is, the sensor 400 can be encapsulated) under controlled ambient conditions. The internal environment can be configured with, for example, a low level of humidity selected to prevent permanent stiction from occurring in the sensor 400 should the movable member 408 collapse before being activated. In some embodiments, the protective layer 430 can be provided with an adhesive 432 protected by an additional peel-off backing layer, allowing the sensor 400 to be affixed to the surface of, for example, a shipping box or food package. The protective layer 430 can comprise metal, plastic, or any other suitable material capable of protecting the internal environment of the sensor 400 from one or more environmental influences.

The sensor 400 can also include one or more weakened areas or perforations 422 running through the substrate 404 to the optical stack 402, to define one or more removable areas 426 of the substrate. A sealing layer 424 is disposed on a side of the substrate 404 and is configured to maintain the internal environment of the sensor 400, by mechanically supporting the air gap and the perforations 422. An encapsulating lid or shell with a perimeter seal (not shown) incorporating the protective layer described above can also be provided which provides mechanical support at the edges of the sensor 400 and which also protects the integrity of the package's internal environment.

Figure 12B:
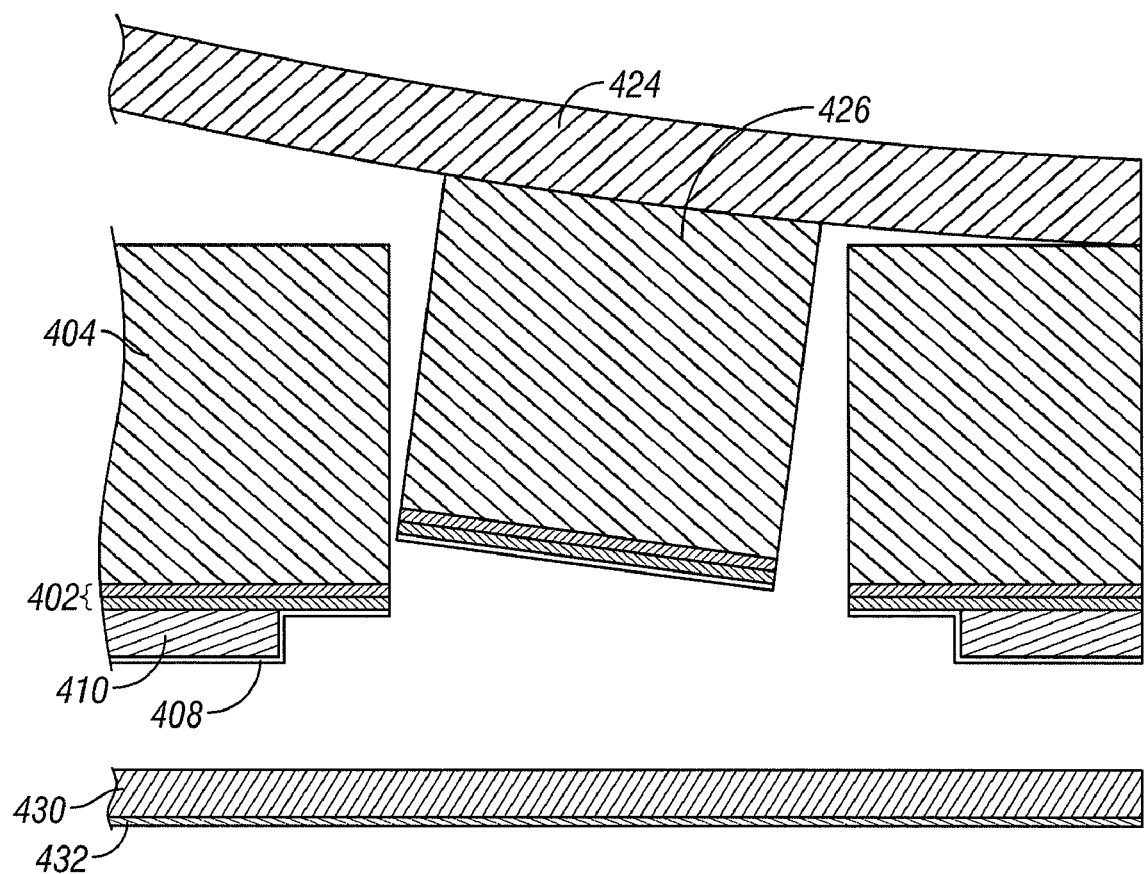
FIG. 12B is a partially cut away cross-section of the sensor of FIG. 11, shown with the sealing layer being removed.

As shown in FIG. 11, the perforations 422 and removable areas 426 are provided in an optically inactive region of the sensor 400, for example in an area between pixels (with a fixed layer 416 instead of a movable layer 408), so as not to interfere with the optical function of the device. The perforations 422 provide weakened areas in the device such that, when the sealing layer 424 is peeled away or otherwise removed from the substrate 404, the removable areas 426, including a portion of the substrate 404 and the underlying layers of the optical stack 402, along with any fixed layer 416, will be broken free from and removed from the surrounding material. This process is illustrated in FIG. 12B. Thus, when the sealing layer 424 is removed, the movable member 408, including any reactive layer 414 disposed thereon, is exposed to the external environment, thus activating the sensor 400. In this way, the internal environment of the sensor 400 is protected from the external environment until activated by a user.

The perforations 422 and/or the removable areas 426 can be configured to expose one or more areas of the sensor 400 to the ambient environment, so as to allow the environment to influence the behavior of the device. The perforations 422 can be empty areas with no structural material, as illustrated in FIG. 11, or can be areas comprising a weakened or frangible material. A plurality of perforations 422 and/or removable areas 426 can be provided in the sensor 400 in a distributed configuration, so as to evenly expose the optically active areas of the sensor 400 to the external environment. The perforation or perforations 422 can be provided in the substrate 404 in any suitable configuration, such as the annular configuration illustrated in FIG. 12A. In certain embodiments, the perforations 422 can be formed by plasma or chemical etching to weaken or remove particular areas on the surface of the substrate 404.

In some embodiments, the substrate and cap can be partially scribed or scored, so as to allow the user to 'snap' off an edge of the sensor package to activate the sensor, while preserving the integrity of the package during shipping and handling. In these embodiments, breaking the score line will open the seal between the substrate and the cap, allowing ambient environmental gases, water vapor, etc. to penetrate into the interferometric cavity and interact with the sensing elements inside.

Figure 13:
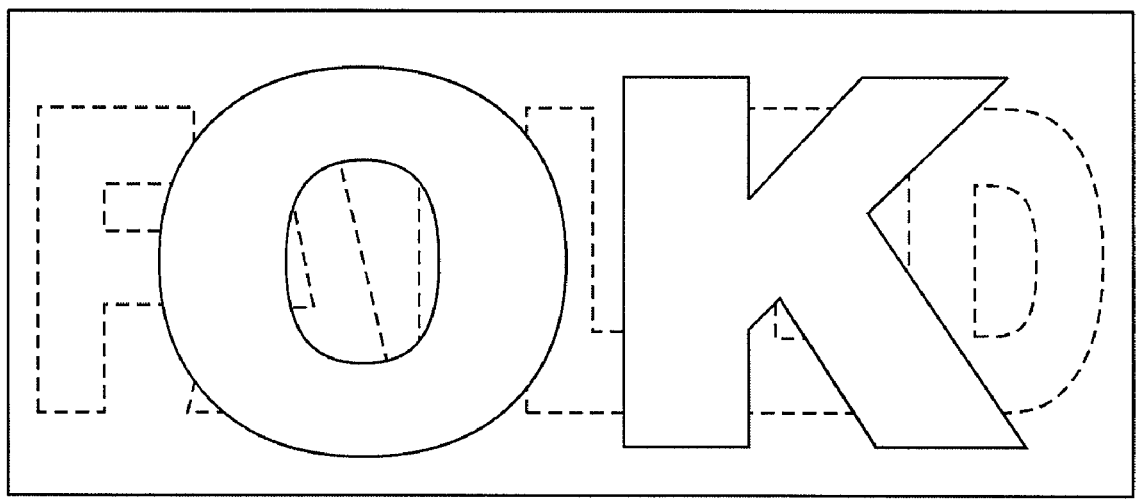
FIG. 13 is a view of a sensor display according to an embodiment, shown in an unactuated state.
Figure 14:
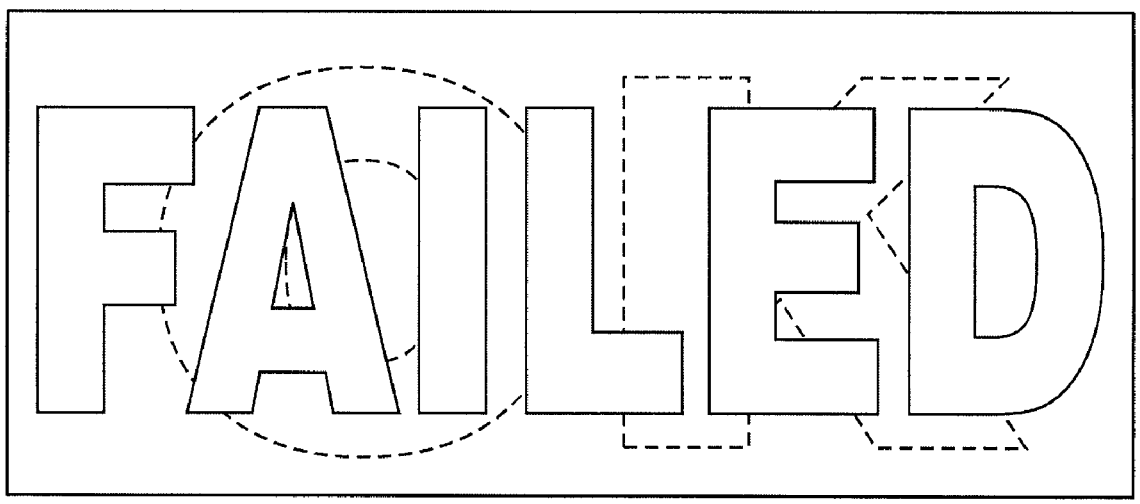
FIG. 14 is a view of the sensor display of FIG. 13, shown in an actuated state.

As mentioned above, embodiments of the invention can be used in multiples and can be configured with varying optical responses to create text, graphic, or color-based sensor displays. FIGS. 13 and 14 illustrate an embodiment comprising an array of sensor devices as described above, configured to display "OK" in an original, uncollapsed state (FIG. 13).

Once exposed to a selected environmental threshold or condition, the array will permanently display "FAILED" (FIG. 14). Since the collapse of the sensor devices in the array will alter the optical response of the devices in a manner detectable by a human observer, no external electronics or apparatus is required to sense the change.

In another embodiment the interferometric modulators can be arranged to display the highest level reached within a certain range, for example with humidity, radiation, temperature, force, etc. Rather than a pass/fail indicator, a range of values may be represented by having images of numbers activate. For example, if the ambient environment of the device reaches 65% humidity, then a portion of the array designed to reach permanent stiction at 65% humidity will do so, with the resulting image showing "65%". Other parts of the array may include other humidity demarcations at appropriate intervals.

While the above detailed description has shown, described and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. A sensor, comprising:
   an interferometric modulator, the modulator configured to permanently actuate in response to a presence of at least one selected chemical, wherein the actuation of the interferometric modulator is visually detectable.

2. The sensor of claim 1, wherein said actuation occurs without requiring application of a voltage across the interferometric modulator.

3. The sensor of claim 1, wherein the interferometric modulator comprises a chemically active layer configured to cause said actuation in response to the presence of said chemical.

4. The sensor of claim 3, wherein the interferometric modulator comprises an optical stack and a movable layer, said chemically active layer being disposed on the movable layer.

5. The sensor of claim 1, further comprising a package configured to seal an internal environment of the interferometric modulator from an external environment, the internal environment being configured to prevent permanent actuation of the modulator, the package comprising at least one removable portion configured to expose the internal environment to the external environment upon removal to activate said sensor.

6. A sensor comprising:
   means for interferometrically modulating light; and
   means for inducing permanent actuation of the light modulating means in response to a presence of at least one selected chemical, wherein said actuation is visually detectable.

7. The sensor of claim 6, wherein said actuation occurs without requiring application of a voltage across the light modulating means.

8. The sensor of claim 6, wherein the inducing means comprises a chemically active layer disposed on a movable member of the light modulating means.

9. The sensor of claim 6, further comprising means for activating the inducing means.

10. The sensor of claim 9, wherein the activating means comprises a removable sealing layer disposed on the light modulating means.

11. A display comprising an array of sensors according to claim 1.

12. A method of manufacturing an interferometric modulator, the method comprising:
    providing a reactive layer on a movable member of the interferometric modulator, the reactive layer being configured to deform sufficiently to cause the interferometric modulator to collapse when exposed to a predetermined chemical; and
    treating the movable member or an optical stack of the interferometric modulator so as to ensure that adhesion will be permanent upon collapse.

13. The method of claim 12, wherein said reactive layer comprises an expansion layer disposed on a side of the movable member facing the optical stack.

14. The method of claim 12, wherein said reactive layer comprises a contraction layer disposed on a side of the movable member facing away from the optical stack.

15. The method of claim 12, wherein said treating comprises driving charge into a surface dielectric film of the optical stack.

16. The method of claim 12, wherein said treating comprises roughening a contact surface of at least one of the movable member or the optical stack.

17. The method of claim 12, wherein said treating comprises coating a contact surface of at least one of the movable member or the optical stack with an adhesive.

18. A method of indicating exposure to an environmental stimulus, the method comprising:
    providing an interferometric modulator having a reactive layer disposed on a movable member of the interferometric modulator, the reactive layer being configured to deform in response to being exposed to a predetermined chemical by an amount sufficient to cause the interferometric modulator to collapse, the interferometric modulator being configured to ensure that said collapse is permanent.

* * * * *